United States Patent
Wackett et al.

(10) Patent No.: US 10,233,437 B2
(45) Date of Patent: Mar. 19, 2019

(54) HYPOCHLORITE RESISTANT CYANURIC ACID HYDROLASES AND METHODS OF USE THEREOF

(71) Applicants: REGENTS OF THE UNIVERSITY OF MINNESOTA, Minneapolis, MN (US); Lawrence P. Wackett, Minneapolis, MN (US); Jennifer L. Seffernick, Minneapolis, MN (US); Kelly Aukema, Minneapolis, MN (US)

(72) Inventors: Lawrence P. Wackett, Minneapolis, MN (US); Jennifer L. Seffernick, Minneapolis, MN (US); Kelly Aukema, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 15/554,392

(22) PCT Filed: Mar. 2, 2016

(86) PCT No.: PCT/US2016/020384
§ 371 (c)(1),
(2) Date: Aug. 29, 2017

(87) PCT Pub. No.: WO2016/141026
PCT Pub. Date: Sep. 9, 2016

(65) Prior Publication Data
US 2018/0044655 A1 Feb. 15, 2018

Related U.S. Application Data

(60) Provisional application No. 62/127,052, filed on Mar. 2, 2015.

(51) Int. Cl.
*C12N 9/86* (2006.01)
*C02F 3/34* (2006.01)
(Continued)

(52) U.S. Cl.
CPC ............... *C12N 9/86* (2013.01); *C02F 3/342* (2013.01); *C12N 1/14* (2013.01); *C12N 1/20* (2013.01);
(Continued)

(58) Field of Classification Search
None
See application file for complete search history.

(56) References Cited

U.S. PATENT DOCUMENTS

| 4,071,409 A | 1/1978 | Messing et al. |
| 4,090,919 A | 5/1978 | Chibata et al. |

(Continued)

FOREIGN PATENT DOCUMENTS

| WO | 2007107981 A2 | 9/2007 |
| WO | 2012116013 A2 | 8/2012 |

OTHER PUBLICATIONS

NCBI Reference Sequence WP_001549947.1, published May 11, 2013.*
(Continued)

*Primary Examiner* — Richard C Ekstrom
(74) *Attorney, Agent, or Firm* — Viksnins Harris Padys Malen LLP

(57) ABSTRACT

The present invention relates to engineered cyanuric acid hydrolase enzymes that are resistant to hypochlorite and compositions and devices comprising such enzymes. The present invention also relates to methods of using these enzymes, compositions and devices for the treatment of a liquid, such as water.

28 Claims, 6 Drawing Sheets
Specification includes a Sequence Listing.

(51) Int. Cl.
    *C12N 15/52*    (2006.01)
    *C12N 1/14*     (2006.01)
    *C12N 1/20*     (2006.01)
    *C02F 103/42*   (2006.01)
(52) U.S. Cl.
    CPC ...... *C12N 15/52* (2013.01); *C12Y 305/02015* (2013.01); *C02F 2103/42* (2013.01); *C02F 2303/185* (2013.01)

(56) References Cited

U.S. PATENT DOCUMENTS

| | | | |
|---|---|---|---|
| 4,258,133 A | 3/1981 | Mirabel et al. | |
| 4,532,040 A | 7/1985 | Meeks et al. | |
| 4,888,285 A | 12/1989 | Nishimura et al. | |
| 4,935,116 A | 6/1990 | Lemire | |
| 5,055,183 A | 10/1991 | Buchan | |
| 5,177,013 A | 1/1993 | Usui et al. | |
| 5,310,469 A | 5/1994 | Cunningham et al. | |
| 5,478,467 A | 12/1995 | Lemire et al. | |
| 5,855,777 A | 1/1999 | Bachand et al. | |
| 5,980,761 A | 11/1999 | Boissie et al. | |
| 5,998,183 A | 12/1999 | Le et al. | |
| 6,257,242 B1 | 7/2001 | Stavridis | |
| 6,325,929 B1 | 12/2001 | Bassett | |
| 6,673,582 B2 | 1/2004 | McTavish | |
| 6,905,733 B2 | 6/2005 | Russell et al. | |
| 6,987,079 B2 | 1/2006 | Wormsbecher | |
| 8,367,389 B2 | 2/2013 | Sadowsky et al. | |
| 2003/0096383 A1 | 5/2003 | Shimizu et al. | |
| 2010/0270228 A1* | 10/2010 | Teichberg | C02F 1/725 210/281 |
| 2011/0127208 A1 | 6/2011 | Sadowsky et al. | |
| 2013/0112608 A1 | 5/2013 | Sadowsky et al. | |
| 2018/0044655 A1* | 2/2018 | Wackett | C12N 9/86 |

OTHER PUBLICATIONS

NCBI Reference Sequence WP_025773350.1, published Jun. 5, 2014.*

UniProtKB/Swiss-Prot Accession No. Q2RGM7, published Oct. 31, 2006.*

Bera, et al., "Structure of the Cyanuric Acid Hydrolase TrzD Reveals Product Exit Channel", Scientific Reports 7, 45277, 9 pages. (2017).

Cantu, et al., "An HPLC Method with UV Detection, pH Control, and Reductive Ascorbic Acid for Cyanuric Acid Analysis in Water", Anal. Chem., 72, 5820-5828 (2000).

Cho, et al., "Crystallization and preliminary X-ray diffraction studies of cyanuric acid hydrolase from Azorhizobium caulinodans", Acta Crystallogr Sect F Struct Biol Cyrst Commun 69(Pt 8), 880-883 (2013).

Cho, et al., "Cyanuric Acid Hydrolase from Azorhizobium caulinodans ORS 571: Crystal Structure and Insights into a New Class of Ser-Lys Dyad Proteins", PLoS One 9, e99349 (2014).

De Souza, et al., "Atrazine Chlorohydrolase from Pseudomonas sp. ADP: Gene Sequence, Enzyme Purification and Protein Characterization", J. Bacteriol., 178, 4894-4900, Supp. p. 695 (1996).

Devers, et al., "Detection and Organization of Atrazine-degrading Genetic Potential of Seventeen Bacterial Isolates Belonging to Divergent Taxa Indicate a Recent Common Origin of Their Catabolic Functions", FEMS Microbiol Lett., 273, 78-86 (2007).

Dodge, et al., "Expanding the cyanuric acid hydrolase protein family to the fungal kingdom", J Bacteriol 195(23), 5233-5241 (2013).

Downes, et al., "Determination of cyanuric acid levels in swimming pool waters by u.v. absorbance, HPLC and melamine cyanurate precipitation", Water Research 18, 277-280 (1984).

Eaton, et al., "Cloning and Comparison of the DNA Encoding Ammelide Aminohydrolase and Cyanuric Acid Amidohydrolase from Three s=Triazine-Degrading Bacterial Strains", J. Bacteriol., 173 No. 3, 1363-1366 (1991).

Fontaine, et al., "A New Type of Glucose Fermentation by Clostridium Thermoaceticum", J. Bacteriol 43, 701-715 (1942).

Fruchey, et al., "On the Origins of Cyanuric Acid Hydrolase: Purification, Substrates, and prevalence of AtzD from Pseudomonas sp. Strain ADP", Appl Environ Microbiol., 69, No. 6, 3653-3657 (2003).

Hennig86, "A PC-DOS Program for Phylogenetic Analysis", Cladistics, 5, 163-166 (1989).

Kaneko, et al., "Complete Genomic Sequence of Nitrogen-fixing Symbiotic Bacterium Bradyrhizobium japonicum USDA110", DNA Research 9, 189-197 (2002).

Karns, "Gene Sequence and Properties of an s-triazine ring-cleavage enzyme from Pseudomonas sp. Strain NRRLB-12227", Appl. Environ. Microbiol., 65, 3512-3517 (1999).

Li, et al., "Thermostable cyanuric acid hydrolase from Moorella thermoacetica ATCC 1-11 39073", Applied and Environmental Microbiology 75(22), 6986-6991 (2009).

Lupas, "The long coming of computational structural biology", Journal of Structural Biology 163, 254-257 (2008).

Marsili, et al., "Microbial Biofilm Voltammetry: Direct Electrochemical Characterization of Catalytic Electrode-Attached Biofilms", Appl Environ Microbiol., 74, 7329-7337 (2008).

NCBI Website, "barbiturase [Catenulispora acidiphila]", NCBI Reference Sequence: WP_012786093.1, 1 page, downloaded Nov. 23, 2013: http://www.ncbi.nlm.nih.gov/protein/WP_012786093.1.

NCBI Website, "barbiturase [Madoestobacter marinus]", NCBI Reference Sequence: YP_006364153.1, 2 pages, downloaded Nov. 23, 2013: http://www.ncbi.nlm.nih.gov/protein/YP_006364153_1.

NCBI Website, "barbiturase [Moorella thermoacetica ATCC 39073]", GneBank: ABC20412.1, (Feb. 1, 2011).

NCBI Website, "barbiturase [Sulfobacillus acidophilus]", NCBI Reference Sequence: WP_014345268_1, DSM 10332, 1 page, downloaded Nov. 23, 2013: http://www.ncbi.nlm.nih.gov/protein/WP_01434528_1.

NCBI Website, "barbiturase [Thermobispora bispora]", NCBI Reference Sequence: WP_013132456_1, 1 page, downloaded Nov. 23, 2013: http://www.ncbi.nlm.nih.gov/protein/WP_0131332456_1.

NCBI Website, "cyanuric acid amidohydrolase [Acidithiobacillus ferrooxidans ATCC 23270]", NCBI Reference Sequence: YP_002425267.1, 1 page, downloaded Nov. 23, 2013: http://www.ncbi.nlm.nih.gov/protein/YP_002425267.1.

NCBI Website, "cyanuric acid amidohydrolase [Acidithiobacillus thiooxidans]", NCBI Reference Sequence: WP_010641892.1, 1 page, downloaded Nov. 23, 2013: http://www.ncbi.nlm.nih.gov/proteinWP 010641892.1.

NCBI Website, "cyanuric acid amidohydrolase, partial [Acidithiobacillus sp. GGI-221]", NCBI Reference Sequence WP_009561038_1, 1 page, downloaded Nov. 23, 2013: http://www.ncbi.nlm.nih.gov/protein/WP_009561038_1.

NCBI Website, "hypothetical protein [Sulfobacillus thermosulfidooxidans]", NCBI Reference Sequence: WP_020373330_1, 1 page, downloaded Nov. 23, 2013: http://www.ncbi.nlm.nih.gov/protein/WP_020373330_1.

NCBI Website, "ring-opening amidohydrolase [Acidithiobacillus caldus]", NCBI Reference Sequence: WP_014003653.1, 1 page, downloaded Nov. 23, 2013: http://www.ncbi.nlm.nih.gov/protein/WP_014003653_1.

NCBI Website, "ring-opening amidohydrolase [Acidithiobacillus ferrivorans SS3]", NCBI Reference Sequence: YP_004783181.1, 1 page, downloaded Nov. 23, 2013: http://www.ncbi.nlm.nih.gov/protein/YP_004783181_1.

NCBI Website, "ring-opening amidohydrolase [Acidithiobacillus ferrooxidans ATCC53993]", NCBI Reference Sequence: YP_002219377.1, 1 page, downloaded Nov. 23, 2013: http://www.ncbi.nlm.nih.gov/protein/YP_002219377.1.

NCBI Website, "ring-opening amidohydrolase [Sulfobacillus acidophilus TPY]", NCBI Reference Sequence: YP_004719285_1, 2 pages, downloaded Nov. 23, 2013: http://www.ncbi.nlm.nih.gov/protein/YP_004719285_1.

NCBI Website, "Sulfobacillus acidophilus DSM 10332", GenBank: AEW05774.1, 2 pages, downloaded Nov. 23, 2013: http://www.ncbi.nlm.nih.gov/protein/AEW05774.1.

(56) References Cited

OTHER PUBLICATIONS

NCBI Website, "ring-opening amidohydrolase [Acidithiobacillus caldus SM-1]", NCBI Reference Sequence: YP_004750255_1, 2 pages, downloaded Nov. 23, 2013: http://www.ncbi.nlm.nih.gov/protein/YP_004750255_1.
Patent Cooperation Treaty, International Searching Authority, Search Report and Written Opinion for PCT/US16/20384, 10 pages, Jun. 10, 2016.
Peat, et al., "Cyanuric acid hydrolase: evolutionary innovation by structural concatenation", Mol Microbiol 88, 1149-1163 (2013).
Pierce, et al., "The complete genome sequence of Moorella thermoacetica (f.Clostridium thermoaceticum)", Environmental Microbiology 10(10), 255-2573 (2008).
Puschner, et al., "Assessment of Melamine and Cyanuric Acid in Cats", J Vet Diagn Invest 19, 616-624 (2007).
Radian, et al., "Silica Gel for Enhanced Activity and Hypochlorite Protection of Cyanuric Acid Hydrolase in Recombinant *Escherichia coli*", mBio 6(6), e01477-15 (2015).
Seffernick, et al., "Ancient Evolution and Recent Evolution Converge for the Biodegradation of Cyanuric Acid and Related Triazines", Appl Environ Microbiol 82(6), 1638-1645 (2016).
Seffernick, et al., "Atrazine Chlorohydrolase from Pseudomonas sp. Strain ADP is a metalloenzyme", Biochemistry, 41, 14430-14437 (2002).
Seffernick, et al., "Defining Sequence Space and Reaction Products within the Cyanuric Acid Hydrolase (AtzD)/ Barbiturase Protein Family", J Bacteriol 194, 4579-4588 (2012).
Seffernick, et al., "Hydroxyatrazine N-ethylaminohydrolase (AtzB): an amidohydrolase superfamily enzyme catalyzing deamination and dechlorinations", J. Bacteriol., 189, 6989-6997 (2007).
Shapir, et al., "Purification, Substrate Range, and Metal Center of AtzC: the N-isopropylammelide aminohydrolase Involved in Bacterial Atrazine Metabolism", J. Bacteriol 184, 5376-5384 (2002).
Shapir, et al., "TrzN from Arthrobacter Aurescens TC1 is a Zinc Amidohydrolase", J Bacteriol., 188, 5859-5864 (2006).
Smith, et al., "Cooperative Catabolic Pathways Within an Atrazine-degrading Enrichment Culture Isolated from Soil", FEMS Microbiol Ecol., 53, 265-273 (2005).

Soong, et al., "Barbiturase, a Novel Zinc-Containing Amidohydrolase Involved in Oxidative Pyrimidine Metabolism", J.Biol. Chem., 277, 7051-7058 (2002).
Suzuki, et al., "Rhizobial Factors Required for Stem Nodule Maturation and Maintenance in Sesbania rostrata-Azorhizobium caulinodans ORS571 Symbiosis", Applied and Environmental Microbiology 73(20), 650-6659 (2007).
Thompson, et al., "CLUSTAL W: Improving the Sensitivity of Progressive Multiple Sequence Alignment Through Sequence Weighting, Position-Specific Gap Penalties and Weight Matrix Choice", Nucleic Acids Res., 22, 4673-4680 (1994).
Uniprot Website, "Ring-opening amidohydrolase—Gloeocapsa sp. PCC7428", K9XGD2_9CHRO, 3 pages, downloaded Nov. 23, 2013: http://www.uniprot.org/uniprot/K9XGD2.
Unitpro Website, "Cyanuric acid amidohydrolase—Azorhizobium caulinodans (strain ATCC 43989 / DSM 5975 / ORS 571", A8ICF8 (A8ICF8_AZ0C5), 4 pages: Downloaded Nov. 23, 2013: http://www.uniprot.org/uniprot/A8ICF8.
Unitpro Website, "Cyanuric acid amidohydrolase—Azorhizobium caulinodans (strain ATCC 43989/DSM 5975/ORS 571)", AZC_3892, 3 pages, downloaded Nov. 23, 2013: http://www.uniprot.org/uniprot/A8IKD2.
Valdes, et al., "Acidithiobacillus ferrooxidans metabolism: from genome sequence to industrial applications", BMC Genomics 9, 597, 24 pages (2008).
Van Der Maarel, et al., "Demethylation of Dimethylsulfoniopropionate to 3-S-methylmercaptopropionate by marine sulfate-reducing bacteria", Appl Environ Microbiol., 62, 3927-3984 (1996).
Yan, et al., "Recent progress on immobilization of enzymes on molecular sieves for reactions in organic solvents", Applied Biochemistry and Biotechnology 101(2), 113-130 (2002).
Yeom, et al., "Bacterial Cyanuric Acid Hydrolase for Water Treatment", Appl Environ Microbiol 81, 666-6668 (2015).
Young, et al., "The genome of Rhizobium leguminosarum has recognizable core and accessory components", Genome Biology 7, R34 (2006).

\* cited by examiner

SEQUENCE LISTING

<160> NUMBER OF SEQ ID NOS: 15

<210> SEQ ID NO 1
<211> LENGTH: 367
<212> TYPE: PRT
<213> ORGANISM: Moorella thermoacetica

<400> SEQUENCE: 1

```
Met Gln Lys Val Glu Val Phe Arg Ile Pro Thr Ala Ser Pro Asp Asp
1               5                   10                  15

Ile Ser Gly Leu Ala Thr Leu Ile Asp Ser Gly Lys Ile Asn Pro Ala
            20                  25                  30

Glu Ile Val Ala Ile Leu Gly Lys Thr Glu Gly Asn Gly Cys Val Asn
        35                  40                  45

Asp Phe Thr Arg Gly Phe Ala Thr Gln Ser Leu Ala Met Tyr Leu Ala
    50                  55                  60

Glu Lys Leu Gly Ile Ser Arg Glu Val Val Lys Val Ala Phe
65                  70                  75                  80

Ile Met Ser Gly Gly Thr Glu Gly Val Met Thr Pro His Ile Thr Val
                85                  90                  95

Phe Val Arg Lys Asp Val Gln Glu Pro Ala Lys Pro Gly Lys Arg Leu
            100                 105                 110

Ala Val Gly Val Ala Phe Thr Arg Asp Phe Leu Pro Glu Glu Leu Gly
        115                 120                 125

Arg Met Glu Gln Val Asn Glu Val Ala Arg Ala Val Lys Glu Ala Met
    130                 135                 140

Lys Asp Ala Gln Ile Asp Asp Pro Arg Asp Val His Phe Val Gln Ile
145                 150                 155                 160

Lys Cys Pro Leu Leu Thr Ala Glu Arg Ile Glu Asp Ala Lys Arg Arg
                165                 170                 175

Gly Lys Asp Val Val Asn Asp Thr Tyr Lys Ser Met Ala Tyr Ser
            180                 185                 190

Arg Gly Ala Ser Ala Leu Gly Val Ala Leu Ala Leu Gly Glu Ile Ser
        195                 200                 205

Ala Asp Lys Ile Ser Asn Glu Ala Ile Cys His Asp Trp Asn Leu Tyr
    210                 215                 220

Ser Ser Val Ala Ser Thr Ser Ala Gly Val Glu Leu Leu Asn Asp Glu
225                 230                 235                 240

Ile Ile Val Val Gly Asn Ser Thr Asn Ser Ala Ser Asp Leu Val Ile
                245                 250                 255

Gly His Ser Val Met Lys Asp Ala Ile Asp Ala Asp Ala Val Arg Ala
            260                 265                 270

Ala Leu Lys Asp Ala Gly Leu Lys Phe Asp Cys Cys Pro Pro Ala Glu
        275                 280                 285

Glu Leu Ala Lys Ile Val Asn Val Leu Ala Lys Ala Glu Ala Ala Ser
    290                 295                 300

Ser Gly Thr Val Arg Gly Arg Asn Thr Met Leu Asp Asp Ser Asp
305                 310                 315                 320

Ile Asn His Thr Arg Ser Ala Arg Ala Val Asn Ala Val Ile Ala
                325                 330                 335

Ser Val Val Gly Asp Pro Met Val Tyr Val Ser Gly Gly Ala Glu His
            340                 345                 350

Gln Gly Pro Asp Gly Gly Pro Ile Ala Val Ile Ala Arg Val
        355                 360                 365
```

<210> SEQ ID NO 2
<211> LENGTH: 1104
<212> TYPE: DNA
<213> ORGANISM: Moorella thermoacetica

<400> SEQUENCE: 2

```
ctacaccctg gcaataacag caattgggcc accgccatca ggcccttgat gctctgcacc      60
accggaaacg tagaccatag gatctcctac cacgctggca ataacagcat ttactactgc     120
tcgcgccgag cgggtatgat tgatatcaga gtcatcaagc atcgtgttac gcctacccct     180
tactgtacca gaagatgcgg cctcagcctt ggccagtaca ttaacgatct tagcaagctc     240
ttctgctggc gggcaacaat caaattttaa accggcatct taagggcag cacgtactgc      300 atcagcgtca atggcatcct tcataacaga gtggcctata accaaatcac tggcactatt     360
ggtagagttt cctactacga taatttcgtc attaagaagt caaccccg ctgacgtcga       420 agccacacta gagtagagat tccagtcatg acaaattgct tcgttgctaa tcttatccgc     480
agatatctcg cccagtgcga gggccactcc gagagctgag cgccacgtg agtaagccat      540 tgatttataa gtgtcattta ccacaacatc tttcccgcgt cgcttggcat cctcaattct     600
ttcagcagtc aaaagcgggc actttatctg aacaaagtga acgtcgcggg gatcatctat     660
ttgggcgtct tcatagcct cttttacagc tcgagccact tcgtttacct gttccatccg      720
gcccaattct tccggcagaa agtcccgcgt aaaagctacg cctactgcca agcgcttttcc    780 tggcttagct ggttcctgga catcttttcg gacaaagaca gtaatgtgcg gcgtcataac     840
accctcagta ccgcctgaca ttataaacgc aactttttt acaacttctt cgcggcttat     900
tcccaatttt tctgctagat acattgctag agattgggta gcaaaaccgc gagtaaaatc     960
gttaacacaa ccattacctt ccgtcttgcc cagaatagct acaatttcag ccggattaat    1020
cttccctgag tcaatcaaag tagccaaccc gctgatatca tcaggtgagg ctgttgggat    1080
acgaaagact tcaacttttt gcat                                            1104
```

<210> SEQ ID NO 3
<211> LENGTH: 367
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

Met Gln Lys Val Glu Val Phe Arg Ile Pro Thr Ala Ser Pro Asp Asp
1               5                   10                  15

Ile Ser Gly Leu Ala Thr Leu Ile Asp Ser Gly Lys Ile Asn Pro Ala
            20                  25                  30

Glu Ile Val Ala Ile Leu Gly Lys Thr Glu Gly Asn Gly Ala Val Asn
        35                  40                  45

Asp Phe Thr Arg Gly Phe Ala Thr Gln Ser Leu Ala Met Tyr Leu Ala
    50                  55                  60

Glu Lys Leu Gly Ile Ser Arg Glu Val Val Lys Lys Val Ala Phe
65                  70                  75                  80

Ile Met Ser Gly Gly Thr Glu Gly Val Met Thr Pro His Ile Thr Val
                85                  90                  95

Phe Val Arg Lys Asp Val Gln Glu Pro Ala Lys Pro Gly Lys Arg Leu
            100                 105                 110

Ala Val Gly Val Ala Phe Thr Arg Asp Phe Leu Pro Glu Glu Leu Gly

```
            115                 120                 125
Arg Met Glu Gln Val Asn Glu Ala Arg Ala Val Lys Glu Ala Met
        130                 135                 140
Lys Asp Ala Gln Ile Asp Asp Pro Arg Asp Val His Phe Val Gln Ile
145                 150                 155                 160
Lys Cys Pro Leu Leu Thr Ala Glu Arg Ile Glu Asp Ala Lys Arg Arg
                165                 170                 175
Gly Lys Asp Val Val Asn Asp Thr Tyr Lys Ser Met Ala Tyr Ser
            180                 185                 190
Arg Gly Ala Ser Ala Leu Gly Val Ala Leu Ala Gly Glu Ile Ser
        195                 200                 205
Ala Asp Lys Ile Ser Asn Glu Ala Ile Cys His Asp Trp Asn Leu Tyr
    210                 215                 220
Ser Ser Val Ala Ser Thr Ser Ala Gly Val Glu Leu Leu Asn Asp Glu
225                 230                 235                 240
Ile Ile Val Val Gly Asn Ser Thr Asn Ser Ala Ser Asp Leu Val Ile
                245                 250                 255
Gly His Ser Val Met Lys Asp Ala Ile Asp Ala Asp Ala Val Arg Ala
            260                 265                 270
Ala Leu Lys Asp Ala Gly Leu Lys Phe Asp Cys Cys Pro Pro Ala Glu
        275                 280                 285
Glu Leu Ala Lys Ile Val Asn Val Leu Ala Lys Ala Glu Ala Ala Ser
    290                 295                 300
Ser Gly Thr Val Arg Gly Arg Asn Thr Met Leu Asp Asp Ser Asp
305                 310                 315                 320
Ile Asn His Thr Arg Ser Ala Arg Ala Val Val Asn Ala Val Ile Ala
                325                 330                 335
Ser Val Val Gly Asp Pro Met Val Tyr Val Ser Gly Gly Ala Glu His
            340                 345                 350
Gln Gly Pro Asp Gly Gly Pro Ile Ala Val Ile Ala Arg Val
        355                 360                 365

<210> SEQ ID NO 4
<211> LENGTH: 367
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Gln Lys Val Glu Val Phe Arg Ile Pro Thr Ala Ser Pro Asp Asp
1               5                   10                  15
Ile Ser Gly Leu Ala Thr Leu Ile Asp Ser Gly Lys Ile Asn Pro Ala
            20                  25                  30
Glu Ile Val Ala Ile Leu Gly Lys Thr Glu Gly Asn Gly Ser Val Asn
        35                  40                  45
Asp Phe Thr Arg Gly Phe Ala Thr Gln Ser Leu Ala Met Tyr Leu Ala
    50                  55                  60
Glu Lys Leu Gly Ile Ser Arg Glu Glu Val Val Lys Lys Val Ala Phe
65                  70                  75                  80
Ile Met Ser Gly Gly Thr Glu Gly Val Met Thr Pro His Ile Thr Val
                85                  90                  95
Phe Val Arg Lys Asp Val Gln Glu Pro Ala Lys Pro Gly Lys Arg Leu
            100                 105                 110
```

Ala Val Gly Val Ala Phe Thr Arg Asp Phe Leu Pro Glu Leu Gly
            115                 120                 125

Arg Met Glu Gln Val Asn Glu Val Ala Arg Ala Val Lys Glu Ala Met
130                 135                 140

Lys Asp Ala Gln Ile Asp Asp Pro Arg Asp Val His Phe Val Gln Ile
145                 150                 155                 160

Lys Cys Pro Leu Leu Thr Ala Glu Arg Ile Glu Asp Ala Lys Arg Arg
                165                 170                 175

Gly Lys Asp Val Val Asn Asp Thr Tyr Lys Ser Met Ala Tyr Ser
            180                 185                 190

Arg Gly Ala Ser Ala Leu Gly Val Ala Leu Ala Leu Gly Glu Ile Ser
        195                 200                 205

Ala Asp Lys Ile Ser Asn Glu Ala Ile Cys His Asp Trp Asn Leu Tyr
    210                 215                 220

Ser Ser Val Ala Ser Thr Ser Ala Gly Val Glu Leu Leu Asn Asp Glu
225                 230                 235                 240

Ile Ile Val Val Gly Asn Ser Thr Asn Ser Ala Ser Asp Leu Val Ile
                245                 250                 255

Gly His Ser Val Met Lys Asp Ala Ile Asp Ala Asp Ala Val Arg Ala
            260                 265                 270

Ala Leu Lys Asp Ala Gly Leu Lys Phe Asp Cys Cys Pro Pro Ala Glu
        275                 280                 285

Glu Leu Ala Lys Ile Val Asn Val Leu Ala Lys Ala Glu Ala Ala Ser
    290                 295                 300

Ser Gly Thr Val Arg Gly Arg Arg Asn Thr Met Leu Asp Asp Ser Asp
305                 310                 315                 320

Ile Asn His Thr Arg Ser Ala Arg Ala Val Val Asn Ala Val Ile Ala
                325                 330                 335

Ser Val Val Gly Asp Pro Met Val Tyr Val Ser Gly Gly Ala Glu His
            340                 345                 350

Gln Gly Pro Asp Gly Gly Gly Pro Ile Ala Val Ile Ala Arg Val
        355                 360                 365

<210> SEQ ID NO 5
<211> LENGTH: 367
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Gln Lys Val Glu Val Phe Arg Ile Pro Thr Ala Ser Pro Asp Asp
1               5                   10                  15

Ile Ser Gly Leu Ala Thr Leu Ile Asp Ser Gly Lys Ile Asn Pro Ala
            20                  25                  30

Glu Ile Val Ala Ile Leu Gly Lys Thr Glu Gly Asn Gly Val Asn
        35                  40                  45

Asp Phe Thr Arg Gly Phe Ala Thr Gln Ser Leu Ala Met Tyr Leu Ala
    50                  55                  60

Glu Lys Leu Gly Ile Ser Arg Glu Glu Val Lys Val Ala Phe
65                  70                  75                  80

Ile Met Ser Gly Gly Thr Glu Gly Val Met Thr Pro His Ile Thr Val
                85                  90                  95

Phe Val Arg Lys Asp Val Gln Glu Pro Ala Lys Pro Gly Lys Arg Leu
            100                 105                 110

```
Ala Val Gly Val Ala Phe Thr Arg Asp Phe Leu Pro Glu Glu Leu Gly
            115                 120                 125

Arg Met Glu Gln Val Asn Glu Val Ala Arg Ala Val Lys Glu Ala Met
        130                 135                 140

Lys Asp Ala Gln Ile Asp Asp Pro Arg Asp Val His Phe Val Gln Ile
145                 150                 155                 160

Lys Cys Pro Leu Leu Thr Ala Glu Arg Ile Glu Asp Ala Lys Arg Arg
                165                 170                 175

Gly Lys Asp Val Val Asn Asp Thr Tyr Lys Ser Met Ala Tyr Ser
            180                 185                 190

Arg Gly Ala Ser Ala Leu Gly Val Ala Leu Ala Leu Gly Glu Ile Ser
        195                 200                 205

Ala Asp Lys Ile Ser Asn Glu Ala Ile Cys His Asp Trp Asn Leu Tyr
210                 215                 220

Ser Ser Val Ala Ser Thr Ser Ala Gly Val Glu Leu Leu Asn Asp Glu
225                 230                 235                 240

Ile Ile Val Val Gly Asn Ser Thr Asn Ser Ala Ser Asp Leu Val Ile
                245                 250                 255

Gly His Ser Val Met Lys Asp Ala Ile Asp Ala Asp Ala Val Arg Ala
            260                 265                 270

Ala Leu Lys Asp Ala Gly Leu Lys Phe Asp Cys Cys Pro Pro Ala Glu
        275                 280                 285

Glu Leu Ala Lys Ile Val Asn Val Leu Ala Lys Ala Glu Ala Ala Ser
        290                 295                 300

Ser Gly Thr Val Arg Gly Arg Arg Asn Thr Met Leu Asp Ser Asp
305                 310                 315                 320

Ile Asn His Thr Arg Ser Ala Arg Ala Val Val Asn Ala Val Ile Ala
                325                 330                 335

Ser Val Val Gly Asp Pro Met Val Tyr Val Ser Gly Gly Ala Glu His
            340                 345                 350

Gln Gly Pro Asp Gly Gly Pro Ile Ala Val Ile Ala Arg Val
        355                 360                 365

<210> SEQ ID NO 6
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gagtaaaatc gttaacagca ccattaccct ccgtcttgcc c                       41

<210> SEQ ID NO 7
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gggcaagacg gaaggtaatg gtgctgttaa cgattttact c                       41

<210> SEQ ID NO 8
<211> LENGTH: 39
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 8
cgagtaaaat cgttaacact accattacct tccgtcttg                          39

<210> SEQ ID NO 9
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
caagacggaa ggtaatggta gtgttaacga ttttactcg                          39

<210> SEQ ID NO 10
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cgagtaaaat cgttaacatc accattacct tccgtcttgc cca                     43

<210> SEQ ID NO 11
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgggcaagac ggaaggtaat ggtgatgtta acgattttac tcg                     43

<210> SEQ ID NO 12
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cgagtaaaat cgttaacaac accattacct tccgtcttgc cca                     43

<210> SEQ ID NO 13
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tgggcaagac ggaaggtaat ggtgttgtta acgattttac tcg                     43

<210> SEQ ID NO 14
<211> LENGTH: 41
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 14
gagtaaaatc gttaacagta ccattacctt ccgtcttgcc c                    41

<210> SEQ ID NO 15
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gggcaagacg gaaggtaatg gtactgttaa cgattttact c                    41
```

HYPOCHLORITE RESISTANT CYANURIC ACID HYDROLASES AND METHODS OF USE THEREOF

PRIORITY OF INVENTION

This application claims priority from U.S. Provisional Patent Application No. 62/127,052 filed Mar. 2, 2015, which is hereby incorporated by reference in its entirety.

GOVERNMENT FUNDING

This invention was made with government support under 2010-ST-061-FD0001-05 MOD 7 awarded by the Department of Homeland Security and IIP-1237754 awarded by the National Science Foundation. The government has certain rights in the invention.

SEQUENCE LISTING

The instant application contains a Sequence Listing which has been submitted electronically in ASCII format and is hereby incorporated by reference in its entirety. Said ASCII copy, created on Mar. 31, 2016, is named 09531.399WO1_SL.txt and is 17,154 bytes in size.

BACKGROUND OF THE INVENTION

There is widespread concern about growing resistance to antimicrobials, but hypochlorite, often referred to as bleach, has been the frontline chemical for a century due to its multiple mechanisms of microbial killing that has prevented widespread resistance. Bleach is used in household products, preventing spread of viruses like Ebola, and in commercial disinfection. For commercial applications especially, chlorinated organic compounds are often added to water to generate bleach in a metered fashion. One such application is the delivery of bleach for swimming pools and industrial water tanks via trichloroisocyanuric acid, commonly known as trichlor. Trichlor stabilizes bleach from light-catalyzed decomposition and so it is the standard mechanism for long-term protection of people in outdoor pools from the spread of infection due to viruses, bacteria and parasites like Giardia. For maintaining the disinfection, it is essential to remove cyanuric acid (CYA) when its concentration rises much above 1 mM (~100 ppm) due to the equilibrium between cyanuric acid and hypochlorite that results in sequestration of most reactive chlorine species at high CYA concentrations.

Developing safe, sustainable disinfection and minimizing water use requires a mechanism to remove cyanuric acid when needed, but CYA is highly stable. While CYA is resistant to acid, base and temperatures of 200° C., some soil microbes easily degrade CYA enzymatically to liberate the three ring nitrogen atoms as ammonia that supports their growth in nitrogen-limiting environments. The microbial enzyme cyanuric acid hydrolase (CAH) hydrolyzes CYA with a $k_{cat}/K_M > 105$ $M^{-1}$ $s^{-1}$. The use of CAH to remove CYA in pools and other disinfection waters has been considered (U.S. Pat. No. 8,367,389); however, one issue hindering the development of a robust system is the sensitivity of cyanuric acid hydrolase to hypochlorite. Hypochlorite is added to pools directly as sodium, lithium, or calcium hypochlorite. It also forms from the hydrolysis of trichlor that is added to pools. So, when cyanuric acid is present, hypochlorite is invariably present. Unfortunately, engineering a hypochlorite resistant biological material is not straightforward.

Accordingly, new compositions and methods for removing CYA from pools and other disinfection waters are needed. In particular, new CAH enzymes (e.g., thermostable) that are resistant to hypochlorite are needed.

SUMMARY OF THE INVENTION

Accordingly, certain embodiments of the invention provide a hypochlorite resistant cyanuric acid hydrolase (CAH) enzyme (e.g., a non-naturally occurring CAH enzyme).

In certain embodiments, the hypochlorite resistant CAH enzyme is thermostable.

Certain embodiments of the invention provide a hypochlorite resistant cyanuric acid hydrolase (CAH) enzyme comprising an amino acid sequence having at least 70% sequence identity to SEQ ID NO:1, SEQ ID NO:3, SEQ ID NO:4 or SEQ ID NO:5.

Certain embodiments of the invention provide an isolated or purified nucleic acid encoding a CAH enzyme described herein.

Certain embodiments of the invention provide an expression cassette comprising a nucleic acid described herein.

Certain embodiments of the invention provide a vector comprising an expression cassette described herein.

Certain embodiments of the invention provide a cell comprising an expression cassette or vector described herein.

Certain embodiments of the invention provide a composition comprising a matrix and a CAH enzyme or cell described herein. In certain embodiments, the matrix comprises silica. Certain embodiments of the invention provide a device for remediation of a liquid comprising a matrix and a CAH enzyme or cell described herein. In certain embodiments, the matrix comprises silica.

Certain embodiments of the invention provide a method of remediating a liquid comprising contacting the liquid from a circulating reservoir with the CAH enzyme, composition, or device described herein to reduce the concentration of cyanuric acid in the liquid.

BRIEF DESCRIPTION OF DRAWINGS

FIG. 1A) Percent activity vs. incubation time. FIG. 1B) Log percent activity vs. incubation time.

FIG. 4A) Comparison of WT protein with C46A and C46S variants. FIG. 4B) Comparison of WT protein with C46V, C46T and C46D variants. FIG. 4C) Overlay of graphs shown in 4A and 4B.

DETAILED DESCRIPTION OF THE INVENTION

Figure 1A:
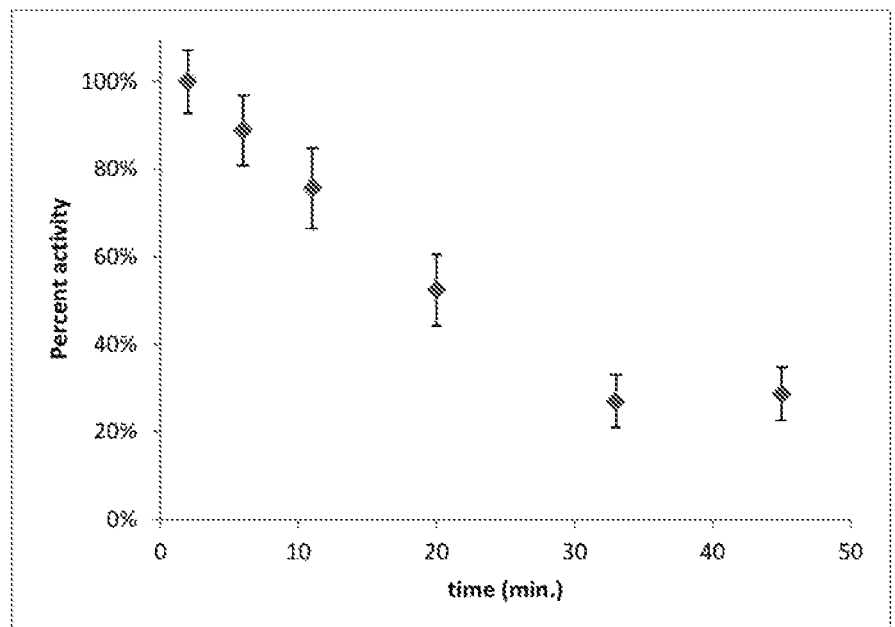
FIGS. 1A-B. Activity of wild-type Moorella CAH in the presence of 1 mM bleach with increasing exposure time.

Hypochlorous acid (HOCl) is a common source of free chlorine. Chemical compounds that release free chlorine are the most commonly used sanitizers in swimming pools and other disinfection waters. Hypochlorous acid, however, is highly unstable, and readily decomposes into inactive breakdown products, such as hydrochloric acid, water and oxygen, via UV radiation-driven photochemical reactions upon exposure to direct sun light, and/or upon exposure to moderate and high temperatures. On a typical summer day, up to 90% of the total active chlorine species are lost within two to three hours. In order to control these effects and preserve the effectiveness of the chlorine, the chlorine-stabilizing agent cyanuric acid (also called s-triazinetrione or isocyanuric acid) is often added to the water. Cyanuric acid, as well as cyanurate salts and various derivatives thereof are compounds which protect the chlorine from the negative effects of UV and heat, and therefore practically reduce the amount of chlorine which needs to be added to the water in order to maintain safe conditions of disinfection. The protection action of these compounds is achieved by the ability of free chlorine ($Cl^+$) to reversibly bind to the nitrogen atoms in the cyanuric acid ring. With a correct dosing, cyanuric acid can reduce the chlorine consumption. However, incorrect balance of cyanuric acid can create an over-protective effect and hence substantially decrease the effectiveness of chlorine as a disinfectant.

Excessive amounts of cyanuric acid drive the equilibrium towards the uptake of free chlorine. Hence, excessive amounts of cyanuric acid cause the chlorine to become progressively over-stabilized, reducing the availability of free chlorine and interfering with its disinfection function. The phenomenon, known as "chlorine-lock", takes place when the concentration of cyanuric acid reaches over 100 ppm (0.77 mM). Chlorine-lock expresses itself similarly to inadequately low chlorine level, in clouding of the water which, apart from an aesthetic nuisance, is a clear indication that the water is no longer safe for use. Once added to the pool or disinfection waters, cyanuric acid does not dissipate or degrade substantially. It is removed from the pool or water reservoir only by splash-out and backwash waste procedures or dilution. Typically, cyanuric acid level is lowered by draining part of the water and diluting the remaining water with fresh water. If the cyanuric acid level exceeds 100 ppm considerably, the pool or other reservoir should be partially or totally drained and have its inner-walls scrubbed (cyanuric acid will sediment on the sides of the pool/reservoir). This time-consuming and water-wasteful process is extremely costly not only in terms of water but also in loss of operational time, additional stabilized chlorine added, and the so far unavoidable reiterative nature of the overall process needed to maintain the balance between the concentration of reactive chlorine species and the concentration of cyanuric acid.

The present invention provides hypochlorite resistant cyanuric acid hydrolase enzymes, compositions and devices for removing excess cyanuric acid, e.g., from pool water, without the need to drain the water and/or diluting the remaining water. By having an enzyme that rapidly degrades cyanuric acid and is resistant to chlorine, commercial enzyme filters that clean pools, spas and other disinfection waters become economically feasible. In certain embodiments, the engineered CAH enzymes are more robust than current forms of the enzyme, enabling less enzyme to be used per treatment, as well as providing enhanced performance.

Certain embodiments of the invention provide a hypochlorite resistant cyanuric acid hydrolase (CAH) enzyme comprising an amino acid sequence having at least 60% sequence identity to SEQ ID NO:1, SEQ ID NO:3, SEQ ID NO:4 or SEQ ID NO:5. In certain embodiments, the amino acid sequence has at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:1, SEQ ID NO:3, SEQ ID NO:4 or SEQ ID NO:5.

As used herein the term "hypochlorite resistant" means the CAH enzyme has at least about 15%, 20%, 25%, 30%, 35%, 40%, 45%, 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% more activity than a corresponding control CAH enzyme (e.g., a corresponding wildtype enzyme) after exposure to hypochlorite under the same conditions.

In certain embodiments, the hypochlorite resistant CAH enzyme is a mutated form of the CAH enzyme derived from *Moorella thermoacetica*, such as from *Moorella thermoacetica* ATCC 39073. An amino acid sequence of a CAH enzyme derived from *Moorella thermoacetica* is shown below as SEQ ID NO:1.

```
                                        (SEQ ID NO: 1)
MQKVEVFRIPTASPDDISGLATLIDSGKINPAEIVAILGKTEGNGCVND

FTRGFATQSLAMYLAEKLGISREEVVKKVAFIMSGGTEGVMTPHITVFV

RKDVQEPAKPGKRLAVGVAFTRDFLPEELGRMEQVNEVARAVKEAMKDA

QIDDPRDVHFVQIKCPLLTAERIEDAKRRGKDVVVNDTYKSMAYSRGAS

ALGVALALGEISADKISNEAICHDWNLYSSVASTSAGVELLNDEIIVVG

NSTNSASDLVIGHSVMKDAIDADAVRAALKDAGLKFDCCPPAEELAKIV

NVLAKAEAASSGTVRGRRNTMLDDSDINHTRSARAVVNAVIASVVGDPM

VYVSGGAEHQGPDGGGPIAVIARV.
```

A nucleic acid molecule encoding SEQ ID NO:1 is shown below as SEQ ID NO: 2.

```
                                        (SEQ ID NO: 2)
CTACACCCTGGCAATAACAGCAATTGGGCCACCGCCATCAGGCCCTTGA

TGCTCTGCACCACCGGAAACGTAGACCATAGGATCTCCTACCACGCTGG

CAATAACAGCATTTACTACTGCTCGCGCCGAGCGGGTATGATTGATATC

AGAGTCATCAAGCATCGTGTTACGCCTACCCCTTACTGTACCAGAAGAT

GCGGCCTCAGCCTTGGCCAGTACATTAACGATCTTAGCAAGCTCTTCTG

CTGGCGGGCAACAATCAAATTTTAAACCGGCATCTTTAAGGGCAGCACG

TACTGCATCAGCGTCAATGGCATCCTTCATAACAGAGTGGCCTATAACC

AAATCACTGGCACTATTGGTAGAGTTTCCTACTACGATAATTTCGTCAT

TAAGAAGTTCAACCCCCGCTGACGTCGAAGCCACACTAGAGTAGAGATT

CCAGTCATGACAAATTGCTTCGTTGCTAATCTTATCCGCAGATATCTCG
```

-continued

```
CCCAGTGCGAGGGCCACTCCGAGAGCTGAGGCGCCACGTGAGTAAGCCA

TTGATTTATAAGTGTCATTTACCACAACATCTTTCCCGCGTCGCTTGGC

ATCCTCAATTCTTTCAGCAGTCAAAAGCGGGCACTTTATCTGAACAAAG

TGAACGTCGCGGGGATCATCTATTTGGGCGTCTTTCATAGCCTCTTTTA

CAGCTCGAGCCACTTCGTTTACCTGTTCCATCCGGCCCAATTCTTCCGG

CAGAAAGTCCCGCGTAAAAGCTACGCCTACTGCCAAGCGCTTTCCTGGC

TTAGCTGGTTCCTGGACATCTTTTCGGACAAAGACAGTAATGTGCGGCG

TCATAACACCCTCAGTACCGCCTGACATTATAAACGCAACTTTTTTTAC

AACTTCTTCGCGGCTTATTCCCAATTTTTCTGCTAGATACATTGCTAGA

GATTGGGTAGCAAAACCGCGAGTAAAATCGTTAACACAACCATTACCTT

CCGTCTTGCCCAGAATAGCTACAATTTCAGCCGGATTAATCTTCCCTGA

GTCAATCAAAGTAGCCAACCCGCTGATATCATCAGGTGAGGCTGTTGGG

ATACGAAAGACTTCAACTTTTTGCAT.
```

In certain embodiments, SEQ ID NO:1 is mutated and the cysteine at residue 46 is replaced with an alanine (C46A) (see, SEQ ID NO:3 below).

```
                                      (SEQ ID NO: 3)
MQKVEVFRIPTASPDDISGLATLIDSGKINPAEIVAILGKTEGNGAVND

FTRGFATQSLAMYLAEKLGISREEVVKKVAFIMSGGTEGVMTPHITVFV

RKDVQEPAKPGKRLAVGVAFTRDFLPEELGRMEQVNEVARAVKEAMKDA

QIDDPRDVHFVQIKCPLLTAERIEDAKRRGKDVVVNDTYKSMAYSRGAS

ALGVALALGEISADKISNEAICHDWNLYSSVASTSAGVELLNDEIIVVG

NSTNSASDLVIGHSVMKDAIDADAVRAALKDAGLKFDCCPPAEELAKIV

NVLAKAEAASSGTVRGRRNTMLDDSDINHTRSARAVVNAVIASVVGDPM

VYVSGGAEHQGPDGGGPIAVIARV.
```

In certain embodiments, SEQ ID NO:1 is mutated and the cysteine at residue 46 is replaced with an serine (C46S) (see, SEQ ID NO:4 below).

```
                                      (SEQ ID NO: 4)
MQKVEVFRIPTASPDDISGLATLIDSGKINPAEIVAILGKTEGNGSVND

FTRGFATQSLAMYLAEKLGISREEVVKKVAFIMSGGTEGVMTPHITVFV

RKDVQEPAKPGKRLAVGVAFTRDFLPEELGRMEQVNEVARAVKEAMKDA

QIDDPRDVHFVQIKCPLLTAERIEDAKRRGKDVVVNDTYKSMAYSRGAS

ALGVALALGEISADKISNEAICHDWNLYSSVASTSAGVELLNDEIIVVG

NSTNSASDLVIGHSVMKDAIDADAVRAALKDAGLKFDCCPPAEELAKIV

NVLAKAEAASSGTVRGRRNTMLDDSDINHTRSARAVVNAVIASVVGDPM

VYVSGGAEHQGPDGGGPIAVIARV.
```

In certain embodiments, SEQ ID NO:1 is mutated and the cysteine at residue 46 is replaced with an glycine (C46G) (see, SEQ ID NO:5 below).

```
                                      (SEQ ID NO: 5)
MQKVEVFRIPTASPDDISGLATLIDSGKINPAEIVAILGKTEGNGGVND

FTRGFATQSLAMYLAEKLGISREEVVKKVAFIMSGGTEGVMTPHITVFV

RKDVQEPAKPGKRLAVGVAFTRDFLPEELGRMEQVNEVARAVKEAMKDA

QIDDPRDVHFVQIKCPLLTAERIEDAKRRGKDVVVNDTYKSMAYSRGAS

ALGVALALGEISADKISNEAICHDWNLYSSVASTSAGVELLNDEIIVVG

NSTNSASDLVIGHSVMKDAIDADAVRAALKDAGLKFDCCPPAEELAKIV

NVLAKAEAASSGTVRGRRNTMLDDSDINHTRSARAVVNAVIASVVGDPM

VYVSGGAEHQGPDGGGPIAVIARV.
```

In certain embodiments, the CAH enzyme is an isolated or purified CAH enzyme.

In certain embodiments, the CAH enzyme is a non-naturally occurring CAH enzyme that is not a product of nature. In certain embodiments, the CAH enzymes described herein comprise markedly different characteristics (e.g., structural, functional and/or other properties) as compared to naturally occurring CAH enzyme counterparts. For example, in certain embodiments, a CAH enzyme is engineered to comprise a non-natural mutation(s) that results in enhanced resistance to hypochlorite, and as a result, is structurally and functionally distinct from its naturally occurring counterpart in its natural state.

As described herein, it was unexpectedly determined that the cysteine residue that is naturally present at position 46 in the CAH enzyme from Moorella thermoacetica may be mutated to enhance the enzyme's resistance to hypochlorite to a surprising degree (see, Example 1). Accordingly, in certain embodiments, the amino acid sequence of the CAH enzyme comprises a mutation at residue 46 (or at a corresponding or alignable residue), whereby the mutation results in enhanced resistance to hypochlorite. As described herein, the term "residue 46" refers to position 46 in the amino acid sequence that corresponds to the CAH enzyme from Moorella thermoacetica (SEQ ID NO:1). Mutations may alternatively be made at an equivalent position in other CAH enzymes and an amino acid that corresponds to, or aligns with, amino acid C46 may be readily determined by one skilled in the art using known techniques and algorithms (e.g., BLAST, ExPASy). The numbering of the amino acids may also vary with other alterations to the amino acid sequence of the enzyme, e.g., other mutations or the inclusion of a peptide tag, and an equivalent amino acid that corresponds to, or aligns with residue 46 may be readily determined by one skilled in the art.

While not intending to be limited by theory, it is currently believed based on modeling that the cysteine at position 46 acts as a gate to the channel leading to the active site of the enzyme and opens to let substrate in and product out. When the cysteine residue is oxidized by hypochlorite, the gate becomes "locked" and access to the active site is blocked. By mutating the gate residue to a, e.g., non-oxidizable amino acid (e.g., alanine, glycine or serine) its function as a gate is retained.

Accordingly, in certain embodiments, the amino acid sequence of the CAH enzyme comprises a mutation at residue 46 (or at a corresponding or alignable residue), wherein cysteine is replaced with an amino acid (e.g., natural or synthetic) that does not block access to the active site of the enzyme and that does not react with hypochlorite to form a reaction product that blocks access to the active site of the enzyme (e.g., cysteine is replaced with a non-oxidizable amino acid). Thus, in certain embodiments, the amino acid sequence of the CAH enzyme comprises an alanine, serine, glycine, dehydroalanine, homoserine or an amino acid with a cyclopropyl side chain or an ethyl side chain at residue 46 (or at a corresponding or alignable residue).

In certain embodiments, the amino acid sequence comprises a non-oxidizable amino acid at residue 46 (or at a corresponding or alignable residue). In certain embodiments, the non-oxidizable amino acid is alanine. In certain embodiments, the non-oxidizable amino acid is serine. In certain embodiments, the non-oxidizable amino acid is glycine.

In certain embodiments, the side chain of the non-oxidizable amino acid is less than or about 109 Angstrom$^3$. In certain embodiments, the amino acid side chain does not block substrate access to the CAH enzyme active site. In certain embodiments, the non-oxidizable amino acid is about the same size or smaller than cysteine. In certain embodiments, the amino acid is not valine or threonine.

In certain embodiments, the amino acid sequence comprises SEQ ID NO:3, SEQ ID NO:4 or SEQ ID NO:5. In certain embodiments, the amino acid sequence comprises SEQ ID NO:3. In certain embodiments, the amino acid sequence comprises SEQ ID NO:4. In certain embodiments, the amino acid sequence comprises SEQ ID NO:5.

In certain embodiments, the amino acid sequence consists of SEQ ID NO:3, SEQ ID NO:4 or SEQ ID NO:5. In certain embodiments, the amino acid sequence consists of SEQ ID NO:3. In certain embodiments, the amino acid sequence consists of SEQ ID NO:4. In certain embodiments, the amino acid sequence consists of SEQ ID NO:5.

In certain embodiments, a hypochlorite resistant CAH enzyme described herein is resistant to hydrogen peroxide ($H_2O_2$).

As described herein, "resistant to hydrogen peroxide" means the CAH enzyme has at least about 15%, 20%, 25%, 30%, 35%, 40%, 45%, 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% more activity than a corresponding control CAH enzyme (e.g., a corresponding wildtype enzyme) after exposure to hydrogen peroxide under the same conditions.

Disinfection by-products that form in water treatment plants often include alkylating agents (e.g., halogenated alkylating agents). Accordingly, in certain embodiments, a hypochlorite resistant CAH enzyme described herein is resistant to an alkylating agent (e.g., a sulfhydryl reactive agent; e.g., iodoacetamide). In certain embodiments, the alkylating agent is a charged alkylating agent (e.g., iodoacetic acid).

As described herein, "resistant to an alkylating agent" means the CAH enzyme has at least about 15%, 20%, 25%, 30%, 35%, 40%, 45%, 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% more activity than a corresponding control CAH enzyme (e.g., a corresponding wildtype enzyme) after exposure to alkylating agent under the same conditions.

In certain embodiments, a hypochlorite resistant CAH enzyme described herein is resistant to a heavy metal (e.g., mercury, e.g., mercury (II) salts).

As described herein, "resistant to heavy metal" means the CAH enzyme has at least about 15%, 20%, 25%, 30%, 35%, 40%, 45%, 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% more activity than a corresponding control CAH enzyme (e.g., a corresponding wildtype enzyme) after exposure to a heavy metal under the same conditions.

In certain embodiments, a hypochlorite resistant CAH enzyme described herein is resistant to inactivation from a Michael addition reaction with, e.g., N-ethylmaleimide.

As described herein, "resistant to inactivation from a Michael addition reaction" means the CAH enzyme has at least about 15%, 20%, 25%, 30%, 35%, 40%, 45%, 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% more activity than a corresponding control CAH enzyme (e.g., a corresponding wildtype enzyme) after exposure to a compound that results in a Michael addition reaction (e.g., N-ethylmaleimide) under the same conditions.

A cyanuric acid hydrolase is an enzyme that specifically hydrolyzes cyanuric acid. As used herein "specifically hydrolyzes" means that less than 1% of the enzyme's activity is on other substrates besides cyanuric acid. As used herein, a "cyanuric acid hydrolase" is an enzyme that hydrolytically catalyzes the ring-opening reaction that converts cyanuric acid to biuret. Cyanuric acid hydrolase enzymes are well known in the art and have been isolated from various sources, some of which were characterized by their amino acid sequence, $K_M$ (Michaelis constant), Vmax, inhibitors thereof, and other biochemical parameters. The Michaelis constant represents the dissociation constant (affinity for substrate) of the enzyme-substrate complex. Low values indicate that this complex is held together very tightly and rarely dissociates without the substrate first reacting to form the product. In order that an enzyme would be used effectively for treating liquids (such as water) in large volumes and rate, the enzyme needs to be an efficient catalyst; hence the biometric parameters of cyanuric acid hydrolase are significant in the context of the present invention. The catalysis parameters of cyanuric acid hydrolase on cyanuric acid, namely $K_M$ values of 25-125 μM as presented herein, signify that these enzymes can be used effectively to reduce the concentration of cyanuric acid in the liquid, such as water, so as to achieve a concentration lower than the chlorine-lock concentration of 100 ppm (corresponding to 0.77 mM). Even at the highest allowable concentration of cyanuric acid in such water, 0.62 mM, the enzyme is highly effective and can produce the desired hydrolysis.

Accordingly, in certain embodiments, the hypochlorite resistant CAH enzyme has a $K_m$ value for cyanuric acid of 25-150 μM. In certain embodiments, the CAH has a $K_m$ value for cyanuric acid of 100-130 μM. In certain embodiments, the CAH has a $k_{cat}$ value for cyanuric acid of 4.8-76 s$^{-1}$.

In certain embodiments, the hypochlorite resistant CAH enzyme is structurally stable (see, U.S. Pat. No. 8,367,389, which discusses structurally stable CAH enzymes, and which is specifically incorporated by reference herein). Sources of cyanuric acid hydrolases include man-made biological sources such as native and/or genetically modified microorganisms, plants and animals, which produce or overproduce the enzyme. As described in U.S. Pat. No. 8,367,389, a class of cyanuric acid hydrolases that are unusually stable at various temperatures was identified. These enzymes are "structurally stable" in that they retain their catalytic activity at a broad temperature range, and can be stored for long periods of time under a wide range of conditions with minimal decrease in enzymatic activity. In certain embodiments, the cyanuric acid hydrolase retains at least about 30% enzymatic activity at a temperature above 25° C. In certain embodiments, the cyanuric acid hydrolase is a thermostable enzyme. In general, thermostable enzymes also have a greater overall stability under a variety of conditions, such as to immobilization, to salt, to solvents, to low osmotic strength, etc. Thermostable enzymes hold their structural elements together more tightly, preventing the protein from irreversibly denaturing.

In certain embodiments, the enzyme is thermostable. In certain embodiments, the CAH is thermostable such that the enzyme retains at least about 30% (e.g., at least about 40%, at least about 50%, at least about 95%, or any other value between 30% and 100%) enzymatic activity at a temperature above 25° C., and has activity up to 70° C. In certain embodiments, the enzyme is stable when stored between room temperature and −80° C. (e.g., between 20° C. and −80° C., or any other value in between) for at least 8 weeks. In certain embodiments, the enzyme is stable for at least about 1 year. In certain embodiments, the enzyme retains enzymatic activity at a pH of from about 5.5 to 10.5.

One example of a structurally stable cyanuric acid hydrolase is from the thermophile *Moorella thermoacetica* ATCC 39073. This enzyme has been cloned, expressed in *Escherichia coli*, and purified to homogeneity. The recombinant enzyme was found to have a broader temperature range and greater stability at both elevated and low temperatures, in comparison to previously described cyanuric acid hydrolases. The enzyme had a narrow substrate specificity acting only on cyanuric acid and N-methylisocyanuric acid. The *M. thermoacetica* enzyme did not require metals or other discernible cofactors for activity. However, as described herein, this WT CAH enzyme is sensitive to hypochlorite.

A "variant" of an enzyme is a sequence that is substantially similar to the sequence of the native enzyme. "Wildtype" or "naturally occurring" or "native" refers to the normal gene, or organism found in nature without any known mutation. Variant amino acid sequences include synthetically derived amino acid sequences, or recombinantly derived amino acid sequences. Generally, amino acid sequence variants of the invention will have at least 40, 50, 60, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) amino acid sequence.

The present invention includes variants of naturally-occurring cyanuric acid hydrolases. By "variant" an enzyme is intended as an enzyme derived from the native enzyme by deletion (so-called truncation) or addition of one or more amino acids to the N-terminal and/or C-terminal end of the native enzyme; deletion or addition of one or more amino acids at one or more sites in the native enzyme; or substitution of one or more amino acids at one or more sites in the native enzyme. The enzyme of the invention may be altered in various ways including amino acid substitutions, deletions, truncations, and insertions. Methods for such manipulations are generally known in the art. For example, amino acid sequence variants of the enzyme can be prepared by mutations in the DNA. Methods for mutagenesis and nucleotide sequence alterations are well known in the art. The substitution may be a conserved substitution. A "conserved substitution" is a substitution of an amino acid with another amino acid having a similar side chain. A conserved substitution would be a substitution with an amino acid that makes the smallest change possible in the charge of the amino acid or size of the side chain of the amino acid (alternatively, in the size, charge or kind of chemical group within the side chain) such that the overall enzyme retains its spatial conformation but may have altered biological activity. For example, common conserved changes might be Asp to Glu, Asn or Gln; His to Lys, Arg or Phe; Asn to Gln, Asp or Glu and Ser to Cys, Thr or Gly. Alanine is commonly used to substitute for other amino acids. The 20 essential amino acids can be grouped as follows: alanine, valine, leucine, isoleucine, proline, phenylalanine, tryptophan and methionine having nonpolar side chains; glycine, serine, threonine, cystine, tyrosine, asparagine and glutamine having uncharged polar side chains; aspartate and glutamate having acidic side chains; and lysine, arginine, and histidine having basic side chains.

As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "comparison window" makes reference to a contiguous and specified segment of an amino acid or polynucleotide sequence, wherein the sequence in the comparison window may comprise additions or deletions (i.e., gaps) compared to the reference sequence (which does not comprise additions or deletions) for optimal alignment of the two sequences. Generally, the comparison window is at least 20 contiguous amino acid residues or nucleotides in length, and optionally can be 30, 40, 50, 100, or longer.

As used herein, "percentage of sequence identity" means the value determined by comparing two optimally aligned sequences over a comparison window, wherein the portion of the polypeptide or polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 70%, 71%, 72%, 73%, 74%, 75%, 76%, 77%, 78%, or 79%, at least 80%, 81%, 82%, 83%, 84%, 85%, 86%, 87%, 88%, or 89%, at least 90%, 91%, 92%, 93%, or 94%, and at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, at least 80%, 90%, or at least 95%.

The term "substantial identity" in the context of a peptide indicates that a peptide comprises a sequence with at least 70%, 71%, 72%, 73%, 74%, 75%, 76%, 77%, 78%, or 79%, 80%, 81%, 82%, 83%, 84%, 85%, 86%, 87%, 88%, or 89%, at least 90%, 91%, 92%, 93%, or 94%, or 95%, 96%, 97%, 98% or 99%, sequence identity to the reference sequence over a specified comparison window. An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

The term "amino acid" includes the residues of the natural amino acids (e.g., Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g., dehydroalanine, homoserine, phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g., acetyl or benzyloxycarbonyl), as well as natural and unnatural amino acids protected at the carboxy terminus (e.g., as a ($C_1$-$C_6$)alkyl, phenyl or benzyl ester or amide; or as an α-methylbenzyl amide). Other suitable amino and carboxy protecting groups are known to those skilled in the art (See for example, T. W. Greene, *Protecting Groups In Organic Synthesis*; Wiley: New York, 1981, and references cited therein) The term also comprises natural and unnatural amino acids bearing a cyclopropyl side chain or an ethyl side chain.

The invention encompasses isolated or substantially purified protein compositions. In the context of the present invention, an "isolated" or "purified" polypeptide is a polypeptide that exists apart from its native environment. The terms "polypeptide" and "protein" are used interchangeably herein. An isolated protein molecule may exist in a purified form or may exist in a non-native environment such as, for example, a transgenic host cell or bacteriophage. For example, an "isolated" or "purified" protein, or biologically active portion thereof, may be substantially free of other cellular material, or culture medium when produced by recombinant techniques, or substantially free of chemical precursors or other chemicals when chemically synthesized. A protein that is substantially free of cellular material includes preparations of protein or polypeptide having less than about 30%, 20%, 10%, 5%, (by dry weight) of contaminating protein. In certain embodiments, an "isolated" or "purified" protein may include cell lysates. When the protein of the invention, or biologically active portion thereof, is recombinantly produced, preferably culture medium represents less than about 30%, 20%, 10%, or 5% (by dry weight) of chemical precursors or non-protein-of-interest chemicals. Fragments and variants of the disclosed proteins or partial-length proteins encoded thereby are also encompassed by the present invention. By "fragment" or "portion" is meant a full length or less than full length of the amino acid sequence of a protein.

Thus, the genes and nucleotide sequences of the invention include both the naturally occurring sequences as well as mutant forms. In certain embodiments, the genes and nucleotide sequences of the invention include mutant forms. Likewise, the polypeptides of the invention encompass naturally occurring proteins as well as variations and modified forms thereof. Such variants will continue to possess the desired activity. In certain embodiments, the polypeptides of the invention encompass variations and modified forms of naturally occurring proteins. The deletions, insertions, and substitutions of the polypeptide sequence encompassed herein are not expected to produce radical changes in certain characteristics of the polypeptide (e.g., the polypeptide would still retain CAH activity; however, the mutations described herein may alter the enzyme's resistance to hypochlorite). However, when it is difficult to predict the exact effect of the substitution, deletion, or insertion in advance of doing so, one skilled in the art will appreciate that the effect will be evaluated by routine screening assays.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). In addition, individual substitutions, deletions or additions which alter, add or delete a single amino acid or a small percentage of amino acids in an encoded sequence are also "conservatively modified variations."

By "portion" or "fragment," as it relates to a nucleic acid molecule, sequence or segment of the invention, when it is linked to other sequences for expression, is meant a sequence having at least 80 nucleotides, more preferably at least 150 nucleotides, and still more preferably at least 400 nucleotides. If not employed for expressing, a "portion" or "fragment" means at least 9, preferably 12, more preferably 15, even more preferably at least 20, consecutive nucleotides, e.g., probes and primers (oligonucleotides), corresponding to the nucleotide sequence of the nucleic acid molecules of the invention.

Nucleic Acids Encoding Hypochlorite Resistant Cyanuric Acid Hydrolases

The present invention includes isolated nucleic acids, expression cassettes and vectors that encode the hypochlorite CAH enzymes described above.

Accordingly, certain embodiments of the invention provide an isolated or purified nucleic acid encoding a CAH enzyme described herein.

Certain embodiments of the invention provide an expression cassette comprising the nucleic acid encoding a CAH enzyme described herein. In certain embodiments, the expression cassette further comprises a promoter, such as a regulatable promoter or a constitutive promoter. In certain embodiments, the promoter is operably linked to the nucleic acid encoding the CAH enzyme. In certain embodiments, the expression cassette further comprises a second nucleic acid encoding a peptide tag. In certain embodiments, the second nucleic acid is operably linked to the nucleic acid encoding the CAH enzyme.

Certain embodiments of the invention provide a vector comprising an expression cassette described herein.

Certain embodiments of the invention provide a cell comprising an expression cassette or a vector described herein.

Certain embodiments of the invention provide a cell lysate derived from a cell described herein.

The term "nucleic acid" and "polynucleotide" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues. A "nucleic acid fragment" is a fraction of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA that can be single- or double-stranded, optionally containing synthetic, non-natural or altered nucleotide bases capable of incorporation into DNA or RNA polymers. The terms "nucleic acid," "nucleic acid molecule," "nucleic acid fragment," "nucleic acid sequence or segment," or "polynucleotide" may also be used interchangeably with gene, cDNA, DNA and RNA encoded by a gene, e.g., genomic DNA, and even synthetic DNA sequences. The term also includes sequences that include any of the known base analogs of DNA and RNA.

"Synthetic" nucleic acids are those prepared by chemical synthesis. The nucleic acids may also be produced by recombinant nucleic acid methods. "Recombinant nucleic acid molecule" is a combination of nucleic acid sequences that are joined together using recombinant nucleic acid technology and procedures used to join together nucleic acid sequences as described, for example, in Sambrook and Russell (2001). As used herein, the term "recombinant nucleic acid," e.g., "recombinant DNA sequence or segment" refers to a nucleic acid, e.g., to DNA, that has been derived or isolated from any appropriate cellular source, that may be subsequently chemically altered in vitro, so that its sequence is not naturally occurring, or corresponds to naturally occurring sequences that are not positioned as they would be positioned in a genome that has not been transformed with exogenous DNA. An example of preselected DNA "derived" from a source would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. Therefore, "recombinant DNA" includes completely synthetic DNA sequences, semi-synthetic DNA sequences, DNA sequences isolated from biological sources, and DNA sequences derived from RNA, as well as mixtures thereof.

Nucleic acid molecules having base substitutions (i.e., variants) are prepared by a variety of methods known in the art. These methods include, but are not limited to, isolation from a natural source (in the case of naturally occurring sequence variants) or preparation by oligonucleotide-mediated (or site-directed) mutagenesis, PCR mutagenesis, and cassette mutagenesis of an earlier prepared variant or a non-variant version of the nucleic acid molecule.

The invention encompasses isolated or substantially purified nucleic acid compositions. In the context of the present invention, an "isolated" or "purified" DNA molecule or an "isolated" or "purified" polypeptide is a DNA molecule that exists apart from its native environment. An isolated DNA molecule may exist in a purified form or may exist in a non-native environment such as, for example, a transgenic host cell or bacteriophage. For example, an "isolated" or "purified" nucleic acid molecule, or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. In one embodiment, the RNA or DNA is "isolated" in that it is free from at least one contaminating nucleic acid with which it is normally associated in the natural source of the RNA or DNA and in one embodiment of the invention is substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell, e.g., in a vector or plasmid. In one embodiment, an "isolated nucleic acid" may be a DNA molecule that is complementary or hybridizes to a sequence in a gene of interest and remains stably bound under stringent conditions (as defined by methods well known in the art). Fragments and variants of the disclosed nucleotide sequences encoded thereby are also encompassed by the present invention. By "fragment" or "portion" is meant a full length or less than full length of the nucleotide sequence encoding the amino acid sequence of a protein.

The term "gene" is used broadly to refer to any segment of nucleic acid associated with a biological function. Thus, genes include coding sequences and/or the regulatory sequences required for their expression. For example, gene refers to a nucleic acid fragment that expresses mRNA, functional RNA, or specific protein, including regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters. In addition, a "gene" or a "recombinant gene" refers to a nucleic acid molecule comprising an open reading frame and including at least one exon and (optionally) an intron sequence. The term "intron" refers to a DNA sequence present in a given gene which is not translated into protein and is generally found between exons.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis that encode the native protein, as well as those that encode a polypeptide having amino acid substitutions. Generally, nucleotide sequence variants of the invention will have at least 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein which encodes a polypeptide also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a polypeptide is implicit in each described sequence.

A "vector" is defined to include, inter alia, any plasmid, cosmid, phage or binary vector in double or single stranded linear or circular form which may or may not be self-transmissible or mobilizable, and which can transform prokaryotic or eukaryotic host either by integration into the cellular genome or exist extrachromosomally (e.g., autonomous replicating plasmid with an origin of replication).

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. The expression of the nucleotide sequence in the expression cassette may be under the control of a constitutive promoter or of an inducible promoter that initiates transcription only when the host cell is exposed to some particular external stimulus. In the case of a multicellular organism, the promoter can also be specific to a particular tissue or organ or stage of development.

Such expression cassettes will comprise the transcriptional initiation region of the invention linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

"Coding sequence" refers to a DNA or RNA sequence that codes for a specific amino acid sequence and excludes the non-coding sequences. It may constitute an "uninterrupted coding sequence", i.e., lacking an intron, such as in a cDNA or it may include one or more introns bounded by appropriate splice junctions. An "intron" is a sequence of RNA which is contained in the primary transcript but which is removed through cleavage and re-ligation of the RNA within the cell to create the mature mRNA that can be translated into a protein.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

"Operably-linked" nucleic acids refers to the association of nucleic acid sequences on single nucleic acid fragment so that the function of one is affected by the other, e.g., an arrangement of elements wherein the components so described are configured so as to perform their usual function. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. Control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

"Naturally occurring," "native" or "wild type" is used to describe an object that can be found in nature as distinct from being artificially produced. For example, a nucleotide sequence present in an organism (including a virus), which can be isolated from a source in nature and which has not been intentionally modified in the laboratory, is naturally occurring. Furthermore, "wild-type" refers to the normal gene, or organism found in nature without any known mutation.

"Homology" refers to the percent identity between two polynucleotides or two polypeptide sequences. Two DNA or polypeptide sequences are "homologous" to each other when the sequences exhibit at least about 75% to 85% (including 75%, 76%, 77%, 78%, 79%, 80%, 81%, 82%, 83%, 84%, and 85%), at least about 90%, or at least about 95% to 99% (including 95%, 96%, 97%, 98%, 99%) contiguous sequence identity over a defined length of the sequences.

Compositions and Devices for Remediation of Liquid

Certain embodiments of the present invention provide compositions for use in the remediation of a liquid, such as water, for example, disinfection waters, e.g., water for use in swimming pools, spas, industrial water tanks, to clean food (e.g., fruit), for military disinfection of drinking water, or for cleaning surgical instruments. The compositions include one or more hypochlorite resistant cyanuric acid hydrolases described above or cell as described herein. In certain embodiments, the composition further comprises a matrix (e.g., a matrix comprising silica). The compositions can be used for treating a liquid in order to maintain a chemical balance in the liquid by reducing the level of cyanuric acid in the liquid.

In certain embodiments, the composition is formulated in pellet form (e.g., as a tablet).

Certain embodiments of the present invention provide devices for use in the remediation of a liquid, such as water, for example, disinfection waters, e.g., water for use in swimming pools, spas, industrial water tanks, to clean food (e.g., fruit), for military disinfection of drinking water, or for cleaning surgical instruments. Certain embodiments of the invention provide a device for remediation of a liquid comprising one or more hypochlorite resistant cyanuric acid hydrolases described herein or a cell described herein or a composition for remediation of a liquid as described above. Certain embodiments of the invention provide a device for remediation of a liquid comprising a matrix and one or more hypochlorite resistant cyanuric acid hydrolases described herein or a cell described herein or a composition for remediation of a liquid as described above.

As described below, the term "enzyme" may be used to refer to an isolated enzyme, an enzyme present in a lysate or a cell that expresses the enzyme.

In certain embodiments, the enzymes (e.g., cells expressing the enzymes) are incorporated in, into, or on the matrix. In certain embodiments, the matrix is water-insoluble. In certain embodiments, the enzymes/cells are incorporated in or on a water-insoluble matrix, which serves as a solid support for the enzyme/cell, namely, it provides a stationary object with respect to the water and the various chemicals dissolved in it. The water-insoluble matrix allows performing a continuous and/or repetitive contact of the treated water with the enzyme/cell, as well as maintaining the enzyme/cell affixed, thus eliminating loss of the enzyme/cell due to leaching out. In certain embodiments, the water-insoluble matrix is granular and/or porous. In certain embodiments, the water-insoluble matrix is an organic matrix or an inorganic matrix. In certain embodiments, the matrix is an organic matrix and the organic matrix comprises plastic, nylon, activated carbon, cellulose, agarose, chitin, chitosan, collagen and/or polystyrene. In certain embodiments, the matrix is an inorganic matrix and the inorganic matrix comprises glass, zeolite, silica, alumina, titania, zirconia, calcium alginate and/or celite. In certain embodiments, the matrix comprises silica.

In certain embodiments, the enzyme/cell expressing the enzyme is encapsulated in a silica-matrix, as described in WO 2012/116013, which is hereby incorporated by reference in its entirety. In certain embodiments, the silica nanoparticles are cross-linked with alkoxysiloxanes (e.g., tetraethoxysiloxane (TEOS)) to encapsulate the enzyme/cell.

In certain embodiments, the device further comprises at least one casing or housing for the matrix. In certain embodiments, the water flows through the at least one casing and contacts the enzyme (e.g., cell expressing the enzyme). In certain embodiments, the device further comprises a permeable layer. In certain embodiments, the enzyme is imbedded in or on the permeable layer.

Many commercially available solid-phase synthesis columns, purification and ion-exchange columns are packed with granular and/or porous water-insoluble and water-permeable matrices that are suitable for protein immobilization applications, or can readily be modified so as to be suitable for protein immobilization, and therefore are suitable for use as the water-insoluble matrix according to the present invention. Such granular and/or porous water-insoluble matrices are well known in the art and are used in various applications such as filtration and chromatography. Representative examples include, without limitation, organic substances such as nylons, polystyrenes, polyurethanes and other synthetic polymers and co-polymers, activated carbon, cellulose, agarose, chitin, chitosan and collagen, and inorganic substances such as beads, filters, cloth, glass, plastic, zeolite, silica, alumina, titania, zirconia, calcium alginate and celite.

Other forms of organic polymers, copolymers and cross-linked derivatives thereof, and inorganic materials such as diatomaceous earths and other types of molecular sieves, typically used in various water filtrations, can be used as a granular and/or porous water-insoluble matrix, according to the present invention, on or in which an enzyme can be incorporated.

The term "incorporated," as used herein, refers to any mode of contact between the water-insoluble matrix and the enzyme (e.g., cell expressing the enzyme) which achieves immobilization of the enzyme with respect to the matrix, thus rendering a biochemically active enzyme insoluble, or in other words immobilized, and in some cases more protected, than the soluble enzyme.

Incorporation of an enzyme (e.g., a cell expressing the enzyme) into or on the matrix can be effected by attachment via any type of chemical bonding, including covalent bonds, ionic (electrostatic) bonds, hydrogen bonding, hydrophobic interactions, metal-mediated complexation, affinity-pair bonding and the like, and/or by attachment via any type of physical interaction such as magnetic interaction, surface adsorption, encapsulation, entrapment, entanglement and the like. The enzyme(s) (e.g., the cell(s) expressing the enzyme(s)) can be incorporated in and/or on physical structural elements of a water-insoluble matrix. In cases where the structural elements of the matrix are granular but not porous, such as, for example, in cases where the matrix is made of solid glass beads or particles, or solid plastic beads or particles, the enzyme(s) is incorporated on the surface of the beads or particles, and the water that flows in the channels between the beads or particles comes in contact with the enzyme(s), thus allowing the amide-containing compounds dissolved in the water to be enzymatically degraded.

In cases where the structural element of the matrix is porous but not granular, such as, for example, in cases where the matrix is extruded zeolite blocks, carbonaceous blocks or solid plastic foam blocks, the enzyme(s) (e.g., cell(s) expressing the enzyme(s)) is incorporated in the cavities, on the inner surface of the innate inter-connected pores and channels which are characteristic to such matrices, as well as on the outer surface of the block, and the water that flows in the inter-connected pores and channels comes in contact with the enzyme(s). In cases where the structural elements of the matrix are granular and porous, such as, for example, in cases where the matrix is zeolite granules or molecular sieves pellets, the enzyme(s) is incorporated on the surface of the granules or pellets and in the inner surface of the pores and channels of these matrices, and the water that flows between the granules or pellets as well as through them comes in contact with the enzyme(s), thus allowing the amide-containing compounds dissolved in the water to be enzymatically degraded.

In certain embodiments, the incorporation of the enzyme (e.g., cell expressing the enzyme) to the water-insoluble matrix is effected by a combination of chemical and physical attachments such as covalent bonding and entanglement.

In certain embodiments of the present invention, the incorporation of the enzyme (e.g., cell expressing the enzyme) to the water-insoluble matrix is effected by covalently attaching the enzyme to the water-insoluble matrix (the solid support) by conventional methods known in the art for enzyme immobilization.

Exemplary immobilization techniques are described for example in U.S. Pat. Nos. 4,071,409, 4,090,919, 4,258,133, 4,888,285, 5,177,013, 5,310,469, 5,998,183, 6,905,733, and 6,987,079, U.S. Patent Application Publication No. 2003/0096383, and in Yan-A-X. et al, 2002, Applied Biochemistry and Biotechnology, Vol. 101(2), pp. 113-130(18); and Ye, Yun-hua et al, 2004, Peptide Science, Vol. 41, pp 613-616, which are incorporated herein by reference. Briefly, protein immobilization by covalent bonding to a solid matrix, according to certain embodiments of the present invention, is based on coupling two functional groups, as these are defined hereinbelow, one within the matrix (e.g., on its surface) and the other within the enzyme (e.g., on its surface) (e.g., cell expressing the enzyme), either directly or via a spacer. The spacer can be, for example, a bifunctional moiety, namely, a compound having at least two functional groups which are capable of forming covalent bonds with functional groups of both the matrix and the enzyme. As used herein, the phrase "functional group" describes a chemical group that has certain functionality and therefore can participate in chemical reactions with other components which lead to chemical interactions as described hereinabove (e.g., a bond formation). The phrase "cross-linking agent," as used herein, refers to a bifunctional compound that can promote or regulate intermolecular interactions between polymer chains, linking them together to create a more rigid structure. Cross-links are bonds linking functional groups of polymers and/or other substances, so as to form intermolecular interactions therebetween and, as a result, a three-dimensional network interconnecting these substances. Cross-linking can be effected via covalent bonds, metal complexation, hydrogen bonding, ionic bonds and the like.

Water-treatment devices that are suitable for use in the context of the present invention are described, for example, in U.S. Pat. Nos. 4,532,040, 4,935,116, 5,055,183, 5,478,467, 5,855,777, 5,980,761, 6,257,242 and 6,325,929, which are incorporated by reference.

Water treatment devices utilized in circulating reservoirs typically form a part of a larger system, which is typically referred to as a water plant. Typical water treatment devices used in water plants of circulating reservoirs exert their designated treatment action when water flows therethrough, either by means of a pump or by gravity. The water flows into the system, enters the device, and passes through a water-permeable and water-insoluble matrix within the device, which effects the designated treatment action, typically filtration of insoluble particulates and objects, chemical exchange of solutes and ions and dissolution and addition of chemicals into the water.

The device containing the composition described herein can therefore be any device, or part of a device through which water flows during the process of treating the water. Such a device can be, for example, one or more of a filter, a filter cartridge, an ion-exchanger, an erosion feeder and the likes, as is exemplified hereinbelow. The device may be a removable device such as a removable filter cartridge. Such a removable device can be manufactured and sold separately as a "replacement" cartridge.

Thus, according to certain embodiments, the composition of the present invention can be added to a water-treatment device having a water-treatment substance embedded therein which effects the originally designated treatment action of these devices, or replace that substance altogether.

The device, according to the present embodiments, can form a part of a comprehensive water treatment system, which exerts other water treatment actions, such as filtration of solid particulates and addition of chemicals. Water that flows through such a water-treatment system also flows through the device presented herein. The system can be designed such that all its water capacity flows through the device, or such that only a part of its water capacity flows therethrough.

Typically, the flow rate can be adjusted per device for the optimal function of the system and every device in it. For an efficient function of the present device, which includes an immobilized active enzyme (e.g., a cell expressing the enzyme), the amount of enzyme, amount of water-insoluble matrix, overall shape of the device and flow-rate need to be designed to as to suit the system's layout, water capacity (power) and the expected rate at which the concentration of an amide-containing compound such as, for example, cyanuric acid, is required to be reduced. The rate of an amide-containing compound reduction depends on the enzymatically catalyzed reaction condition, e.g., temperature, pH, ionic strength and, in relevance to this case, water flow. All the above mentioned parameters are considered while designing the device.

The incorporation of enzymes (e.g., cells expressing the enzyme) to water-insoluble matrices is typically measured in international units of activity. An international unit (IU) of an enzyme is defined as the amount of enzyme that produces one micromole of a reaction product in one minute under defined reaction conditions. The amount of IU which can be incorporated to a matrix depends on the type of matrix and incorporation technique, surface area of the matrix, the availability and chemical reactivity of functional groups suitable for conjugation in both the enzyme and the matrix, and on the residual enzymatic activity subsequent to the incorporation process. Typical enzyme load ranges from a few IU to hundreds of IU of an enzyme per $cm^3$ of matrix material. An optimal load, namely, the optimal amount of enzyme to be incorporated per a unit volume of water-insoluble matrix material, is an example of one parameter that is considered while designing the device.

The water-treatment device presented herein is shaped and sized, and its through-flow is designed, so as to achieve optimized efficacy in reducing the concentration of the desired amide-containing compound (e.g., cyanuric acid). For example, using the enzymatic catalysis parameters presented hereinabove for cyanuric acid hydrolases, one can calculate that for a water quantum of 100 cubic meters, 250 mg of cyanuric acid hydrolase is capable of treating this water quantum by decreasing the cyanuric acid concentration from 100 ppm to 50 ppm within a time period of 20 hours. Considering typical water pumps used in water treatment systems of pools, which can transfer an average of 11 cubic meters per hour, this water quantum will be treated by 250 mg of cyanuric acid amidohydrolase once in 9.09 hours and more than twice in 20 hours, which is an acceptable rate of cyanuric acid degradation.

A reduction of 50 ppm in cyanuric acid concentration translates to approximately 50 grams of cyanyric acid (about 0.4 moles) per cubic meter of water at chlorine-lock conditions. Therefore, about 280 IU of cyanuric acid amidohydrolase are required in order to reduce the concentration of cyanuric acid in one cubic meter of water within a time period of 24 hours.

As used herein, the term "about" means±10%.

Thus, according to certain embodiments of the present invention the amount of cyanuric acid hydrolase required to treat one cubic meter of water within a time period of 24 hours ranges from 0.5 mg to 10 mg per, preferably 1 to 5, and more preferably the amount of cyanuric acid amidohydrolase is at least 2.5 mg per one cubic meter of treated water.

As mentioned hereinabove, certain embodiments of the invention provide a device for remediation of a liquid comprising a matrix and a CAH enzyme described herein (e.g., a cell expressing a CAH enzyme). In certain embodiments, the device further comprises a casing or housing for the matrix. In certain embodiments, the water flows through the at least one casing and contacts the enzyme. For example, in certain embodiments, the device may be a flow through reactor, a tea-bag-type device as described below, a skimmer that moves around the top of a liquid (e.g., water, e.g., a pool), or a sand bed filter.

The casing may be used so as to avoid sweeping of the composition-of-matter by the water passing through the device. Another purpose of a casing is to form the desired shape and cross-section of the device, which will optimize its function and maintain a continuous, void-free bed of the composition-of-matter presented herein. The casing material is preferably selected so that it is suitable for water high-pressure, and is typically water-insoluble and water-tight. Furthermore, the casing material is preferably selected so that it is inactive and stable with respect to water and the chemicals that are typically found in circulating reservoirs. Examples for suitable casing materials include, without limitation, plastic (e.g., mesh), galvanized metal and glass.

In preferred embodiments, the device for water treatment of the present invention includes a casing with two parallel perforated faces, constituting a semi-closed compartment, whereby the composition presented herein fills, or partially fills the compartment. The casing thus has one perforated face for a water inlet, and the other perforated face for a water outlet. The water to be treated (containing the amide-containing compound(s)) enters the inlet, passes through the compartment containing the composition, and comes in contact with the permeable and water-insoluble matrix having the enzyme(s) (e.g., cells expressing the enzyme) incorporated therein or thereon.

In certain embodiments, the device for remediation of a liquid comprises a mesh or porous casing, wherein the casing forms a compartment (e.g., a mesh or porous bag, e.g., a mesh or porous bag similar to a tea bag), whereby the enzyme (e.g., cells expressing the enzyme) and matrix (e.g., matrix encapsulated cells) fills or partially fills the compartment of the mesh/porous casing. The device may be placed in a liquid (e.g., water, e.g., a pool) and natural diffusion processes allow the liquid to permeate the casing and contact the enzyme (e.g., cell expressing the enzyme), thereby resulting in the degradation of cyanuric acid.

In certain embodiments, the device may include an immobilizing matrix that has a permeable layer. Such an enzyme-containing matrix could serve as a stationary phase for the reservoir's water.

Other exemplary devices for water treatment according to certain embodiments of the present invention may be a filter cartridge, similar to that disclosed, for example, in U.S. Pat. No. 6,325,929, and containing, as the composition, an extruded solid, water-permeable carbonaceous material block as a water-insoluble matrix and one or more amidohydrolase enzyme(s) incorporated in and on the carbonaceous block.

Methods of Remediating Water

Certain embodiments of the present invention provide devices and compositions for use in the remediation of water, for example, disinfection waters, e.g., water for use in swimming pools, spas, fountains, industrial water tanks, to clean food (e.g., fruit), for military disinfection of drinking water, or for cleaning surgical instruments. In certain embodiments, the method involves the treatment of water with the enzymes, compositions or devices described above. In certain embodiments, in order for the treatment to be effective, it is desirable that the water flow at a certain rate so as to come in contact with an effective amount of the hydrolase for a certain period of time.

Certain embodiments of the invention provide a method of remediating a liquid comprising contacting the liquid from a circulating reservoir with the CAH enzyme (e.g., a cell expressing the CAH enzyme), composition, or device described herein to reduce the concentration of cyanuric acid in the liquid.

In certain embodiments, the enzyme or the cell expressing the enzyme is added directly to a liquid for remediation (e.g., water, e.g., drinking water, water used in foods or water used to clean food, such as fruit).

In certain embodiments, the enzyme is present in pellet form (e.g., a tablet) (e.g., for remediation of drinking water).

In certain embodiments, the method involves adding the CAH enzyme to a liquid, such as water, in the form of a free enzyme or free cell expressing the enzyme, or can be present as part of a device or part of a device through which water flows through or over during the process of treating the water. In certain embodiments, the liquid is contacted with the device described hereinabove by passing the water over or through the device. In certain embodiments, the liquid flows through the device. In certain embodiments, the liquid treatment is effected during a time period of 20 hours or less. In certain embodiments, the passing of the liquid through the device is effected at a flow rate of at least 10 cubic meters per hour. In certain embodiments, the liquid is water.

The phrase "circulating reservoir," as used herein, refers to a structure for holding a relatively large amount of water. The relatively large amount of water means that the water is not replaced after every use, or rarely replaced in general for a long period of time in terms of months and hence maintaining the water is typically achieved by a circulating procedure. In order to maintain the water, it is at least partially pumped or otherwise transferred out of the structure and then back into the reservoir by means of a water transferring device such as, for example, a pump, while being passed via a water treatment plant. Typical, presently used, water treatment plants include water treatment devices, such as, for example, sensors, detectors, heaters, coolers, chemical feeders, chemical exchangers and filters of various purposes and designs.

In certain embodiments the circulating reservoirs are public and/or private reservoirs that are used by humans for hygiene, sports, professional training, recreation, amusement, therapeutic and general bathing and for ceremonial and aesthetic purposes, and include, without limitation, pools, artificial ponds and lakes, swimming pools, spas, hot tubs, whirlpool baths, industrial water tanks, fountains and waterslides. The water treatment system that houses the device and effect water flow through the device by means of, for example, water pumps, distribution manifolds, hoses and pipes, spigots and valves.

In certain embodiments of the invention, the water treatment is effected by reducing a concentration of cyanuric acid in the water. As discussed above, chlorine-lock occurs when the concentration of cyanuric acid reaches 100 ppm, rendering the quality of the water in the circulating reservoir unacceptable. In general, water needed to be treated is generally at about 50-200 ppm, with a goal of reduces levels below about 30 ppm. Thus, in certain embodiments, the method acts to reduce the concentration of cyanuric acid in the water, subsequent to the treatment, to less than about 100 ppm. In certain embodiments, the concentration of cyanuric acid in the liquid subsequent to treatment is less than about 100 ppm. In certain embodiments, the concentration of cyanuric acid in the water, subsequent to the treatment, ranges from about 70 ppm to about 30 ppm.

In certain embodiments, the amount of the hypochlorite resistant cyanuric acid hydrolase is at least about 2.5 mg per one cubic meter of the liquid (e.g., water).

In addition to treating the water of circulating reservoirs in order to reach the desired concentration of cyanuric acid in the water, in certain embodiments the desired effect of water treatment would be achieved within a relatively short period of time. The time period should be minimized so as to avoid loss of operational time of the circulating reservoir, and to avoid the risk of reaching chlorine-lock due to the continuous addition of stabilized sanitizers. The length of the time period within which the treatment takes place depends on the amount of water to be treated, the capacity of the water-treatment system and the amount and the catalytic efficiency of the enzyme, as discussed hereinabove.

To demonstrate an exemplary implementation of the method of treating water according to the present invention, one can consider an exemplary circulating reservoir such as an Olympic swimming pool. An Olympic swimming pool that meets international standards as defined by The International Swimming Federation, must be 50 meters in length by 25 meters wide by at least 2 meters in depth. Among other standards, the water must be kept at 25-28° C. and the lighting level at greater than 1500 lux. There are thus at least 2500 cubic meters of water (660,430 U.S. liquid gallons) which must be treated in a standard Olympic pool.

Using the calculation for the sufficient amount of cyanuric acid hydrolase needed to treat 100 cubic-meters of water, i.e., to reduce the cyanuric acid concentration from 100 ppm to 50 ppm within about 20 hours, as presented hereinabove, the water of an Olympic pool in a state of chlorine-lock should be passed twice through one or more devices, as presented herein, and be brought in contact with a composition-of-matter comprising cyanuric acid hydrolase, according to the present invention. The molecular weight of cyanuric acid is 129.07, so 50 ppm of a 100,000 L pool has 38.7 moles of cyanuric acid. Assuming the enzyme had 10 μmol/min/mg specific activity and contact time was 1200 minutes, then 3.2 g of enzyme would be required. This assumes that the enzyme had infinite number of turnovers and that it retained its original specific activity. This would be static contact time. With water flowing through the filter, the contact time would really be less than this. Basically, it would be 3870 divided by the number of minutes the water was in contact with the enzyme, in order to give the number of grams of enzyme needed. If one assumes that the water is pumped through the filter two times, then 1935 divided by the number of minutes the water was in contact with the filter on each pass would give the number of grams of enzyme needed. For hypothetical sake, if one had a filter with a 5 minute contact time on each pass, then for two passes, one would need 397 grams of enzyme with a specific activity of 10 μmol/min/mg. If it was a one minute contact time then for the same two passes, one would need 1935 grams of enzyme.

The invention will now be illustrated by the following non-limiting Example.

EXAMPLE 1

Rendering a Useful Enzyme for Maintaining Chlorine Disinfection More Useful by Making it Resistant to Chlorine As described herein, cyanuric acid hydrolase (CAH) may be used to increase chlorine disinfection in swimming pools. The most efficacious method for some pools is to use the enzyme to remove low levels of cyanuric acid continuously. However, it has been found that the CAH enzyme derived from *Moorella thermoacetica*, which has been shown to be structurally stable, is inactivated by the chlorine disinfection agent, hypochlorite. Accordingly, certain embodiments of the present invention describe making the enzyme hypochlorite (i.e., chlorine, or bleach) resistant. As described below, it was unexpectedly determined that the cysteine residue position 46 in the CAH enzyme may be mutated to enhance the enzyme's resistance to hypochlorite to a surprising degree.

Introduction

Facing increasing concerns over water supply and safety, there is a need for sustainable methods for water disinfection. Bleach (hypochlorite) and chlorinated chemicals that generate bleach in solution are used for water disinfection for the majority of Earth's population. Water chlorination is the single major advancement in civilization that has allowed human society to move past the days of the Black Death and other rampant infectious diseases that killed most children prior to their fifth birthday. Water chlorination is not only used for drinking water, but also for industrial and recreational waters. Thus, this is a very widespread and crucial process for modern civilization.

Chlorinating agents such as trichloroisocyanuric acid (trichlor) are routinely added to recreational waters (swimming pools and spas) and industrial waters to maintain long-term chlorine disinfection by allowing a slow and steady production of hypochlorite when the chlorine slowly releases off the trichlor. Over time however, chlorine is lost from the pool or spa by spontaneous chemical reactions, cyanuric acid (CYA) accumulates, and high levels of CYA decrease the efficacy of the disinfectant by sequestering chlorine onto the cyanuric acid. As described herein, a process to use the enzyme cyanuric acid hydrolase (CAH) to remove CYA from waters, thus restoring the disinfection power, has been developed. However, if the water being treated contains hypochlorite disinfectant, the enzyme will be inactivated. This is particularly a problem for home pools where it would be most desirable to continuously treat water with CAH to remove CYA as it accumulates. Under those conditions, the enzyme is continuously exposed to chlorine and will be destroyed in too short a time to be useful. Specifically, the same agent (hypochlorite) that kills bacteria and viruses by oxidizing their proteins, membranes and nucleic acids, will oxidize and destroy cyanuric acid hydrolase through oxidation of its amino acid residues. Thus, it is important that the enzyme be protected from inactivation by the hypochlorite.

As described in detail below, it has been found that hypochlorite inactivation of CAH proceeds through first order kinetics, suggesting that there is one key residue oxidized by bleach to inactivate activity. After examination of the crystal structures of two cyanuric acid hydrolases (Cho et al. 2014, Peats et al. 2014) and additional experimentation, it was determined that oxidation of *Moorella thermoacetica* CAH cysteine 46 inactivates the enzyme by blocking substrate access to the active site. To engineer increased bleach resistance in *Morella thermoacetica* cyanuric acid hydrolase (CAH), cysteine 46 was substituted with alanine or serine. The CAH C46A and C46S proteins are largely resistant to inactivation by bleach. Substitution with amino acids with larger side chains, such as valine or threonine, or with oxidized side chains, such as aspartic acid, resulted in severely reduced CAH activity. The use of glycine residues would very likely produce a resistant enzyme that is highly active.

As described below, the bleach-resistant enzyme variants have also been tested for their ability to resist other inactivating agents (e.g., additional oxidants and sulfhydryl reactive reagents).

Results

Engineering Increased CAH Bleach Resistance

Figure 1B:
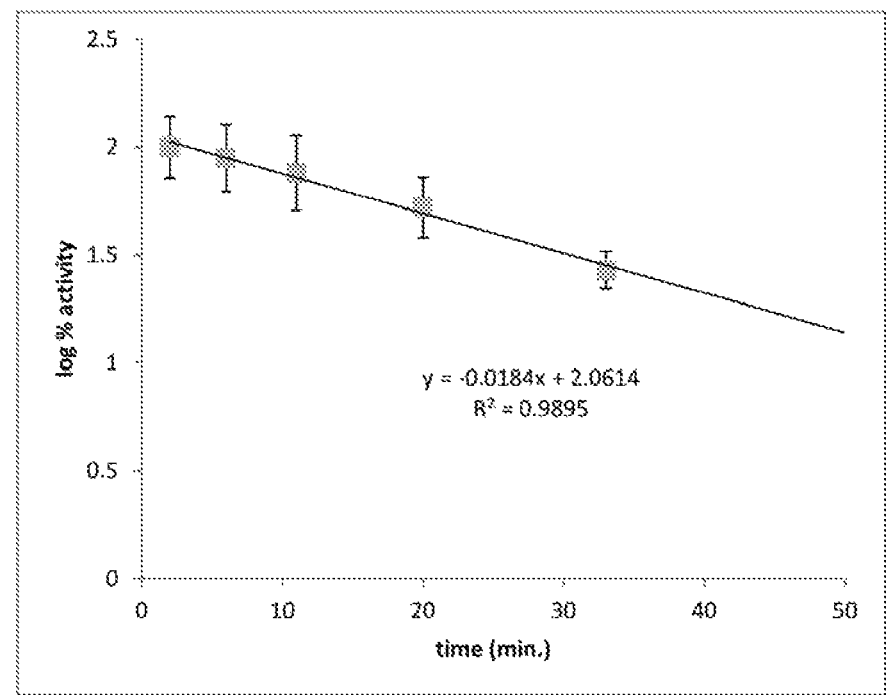

Bleach is known to oxidize a wide range of amino acids and, in general, is thought to inactivate enzyme activity largely through protein unfolding caused by the oxidation of multiple amino acid side chains. To investigate hypochlorite inactivation of *Moorella* CAH, enzyme activity was measured with increasing exposure to bleach (FIG. 1A). Plotting the data as log percent activity over time revealed a linear relationship (FIG. 1B) indicating that bleach inactivation of CAH proceeds by first order kinetics. This kinetic result suggests that at low concentrations of bleach, the oxidation of one amino acid is responsible for loss of activity.

Figure 2:
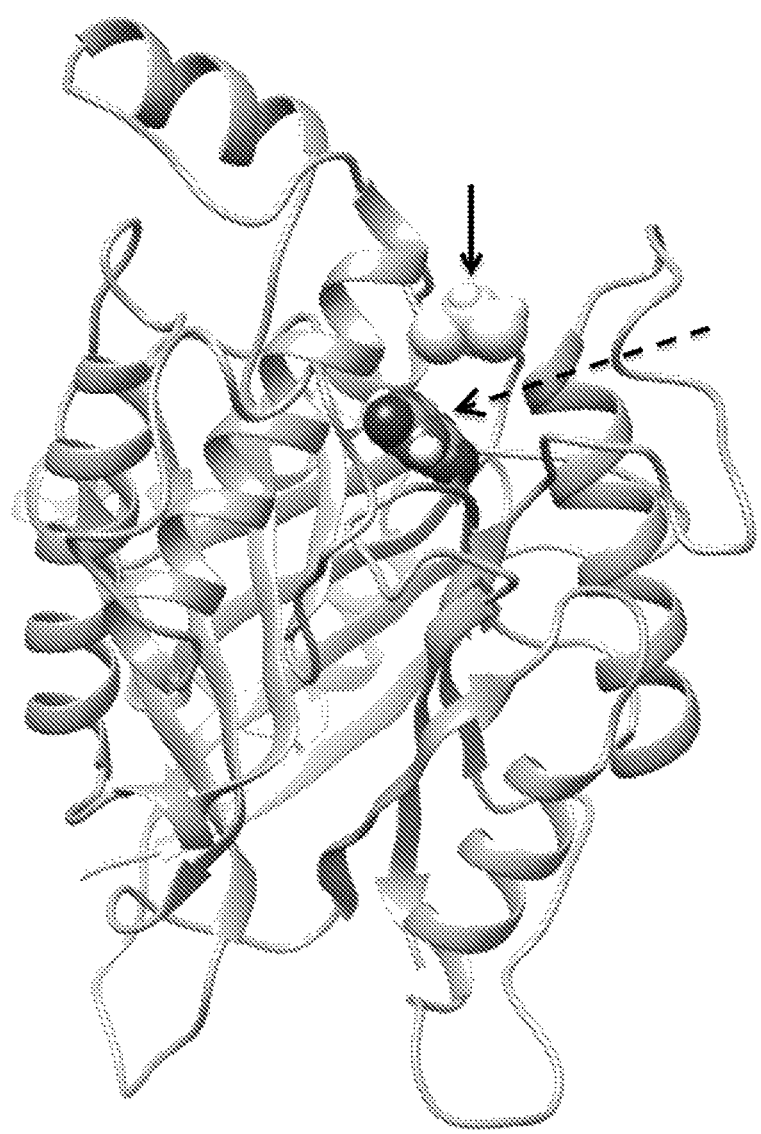
FIG. 2. A modelled side view of a CAH enzyme showing barbituric acid (an analog of cyanuric acid) bound at the active site (spheres; dashed arrow) and the location of cysteine 46 (spheres; solid arrow) in the channel leading to the active site.

Using the X-ray structures of cyanuric acid hydrolases, a homology model of the *Moorella* enzyme was built. Using the structural model, the CAH active site and surrounding residues for oxidizable amino acids that may be the site of oxidation responsible for inactivation of the enzyme were studied. The presence of a cysteine residue (C46) near the active site was observed and it was deduced that the cysteine could be oxidized by hypochlorite to produced sulfenic, sulfinic and sulfonic acids (FIG. 2). The oxidized sulfur groups, based on the homology model, would block the channel to the active site. This would prevent the substrate from entering the active site and shut down enzyme activity. Since this would happen with the oxidation of the cysteine alone, the expected inactivation would follow first order kinetics. Replacing this cysteine with non-oxidizable, yet similarly-sized or smaller, amino acids would prevent enzyme inactivation and not disrupt activity. Loss of enzyme activity upon substitution of C46 to aspartic acid, an oxidation mimic, supports this hypothesis (Table 1).

TABLE 1

Specific activity of *Moorella thermoacetica* CAH.

| CAH | Specific activity[a] | Percent Error |
|---|---|---|
| WT | 26.9291 | 7.3% |
| C46A | 10.03298 | 2.8% |
| C46S | 6.971889 | 3.7% |
| C46T | 0.484122 | 15.3% |
| C46V | 0.143382 | 5.5% |
| C46D | 0.162172 | 6.8% |

[a]$\mu mol\ min^{-1}\ mg^{-1}$

Figure 3:
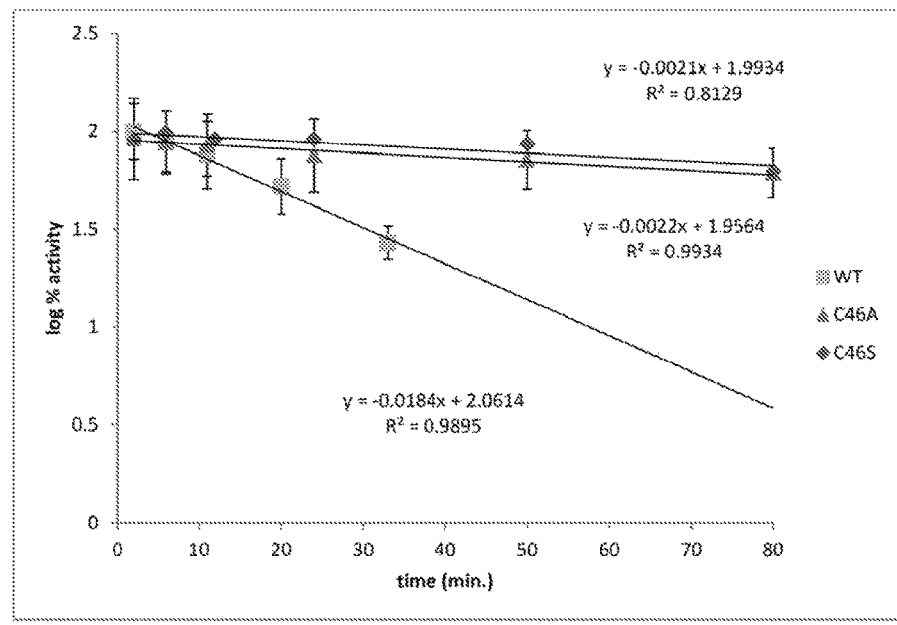
FIG. 3. Moorella CAH C46A and C46S exhibit increased resistance to bleach exposure.

Using site-directed mutagenesis, C46 was changed to alanine and serine. Both residues have side chains of smaller or equal size to cysteine. Importantly both also have non-oxidizable side chains. It was determined that bleach sensitivity (FIG. 3) for both of the substituted proteins compared to the wild-type enzyme, and found that both protein variants are essentially resistant to bleach. In both cases the overall activity of the protein is reduced (Table 1). To determine the range of substitutions able to provide protection from bleach inactivation while retaining enzyme activity, substitutions of C46 to threonine and valine was tested. Both of these side chains are larger than cysteine, but are non-oxidizable. Neither protein retained sufficient activity to pursue further (Table 1). No additional natural amino acids have smaller side chains than the ones tested here with the exception of glycine. Based on sequence alignments of CAHs, it is reasoned that substitution of C46 to glycine may also provide protection from bleach while not severely compromising activity as the homologus *Bradyrhizobium japoncium* USDA 110 AtzD protein has a glycine in place of the cysteine. Purified Brady AtzD had CAH activity and was approximately 5-fold more resistant to bleach (data not shown).

Secondary Structure and Thermal Stability

Figure 4A:
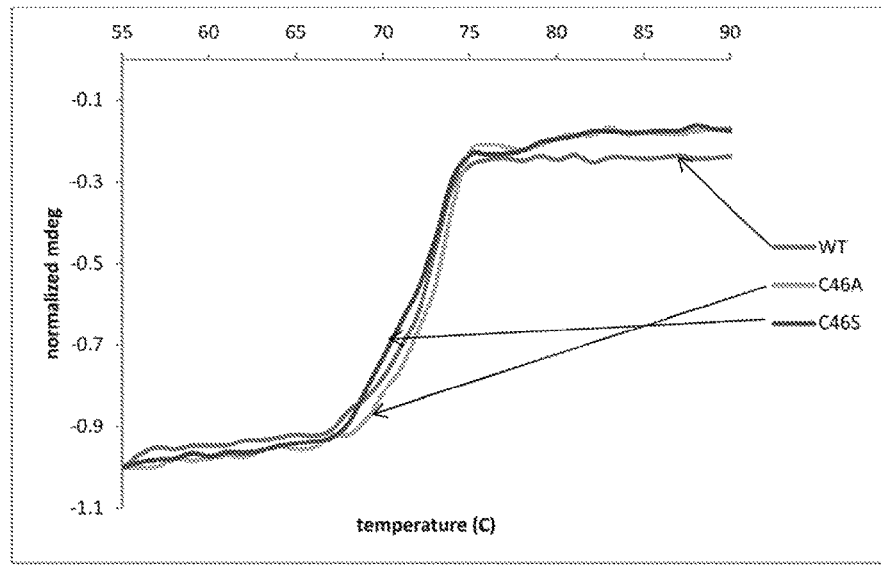
FIGS. 4A-C. Comparison of thermal melting curves for WT protein and variants.
Figure 4B:
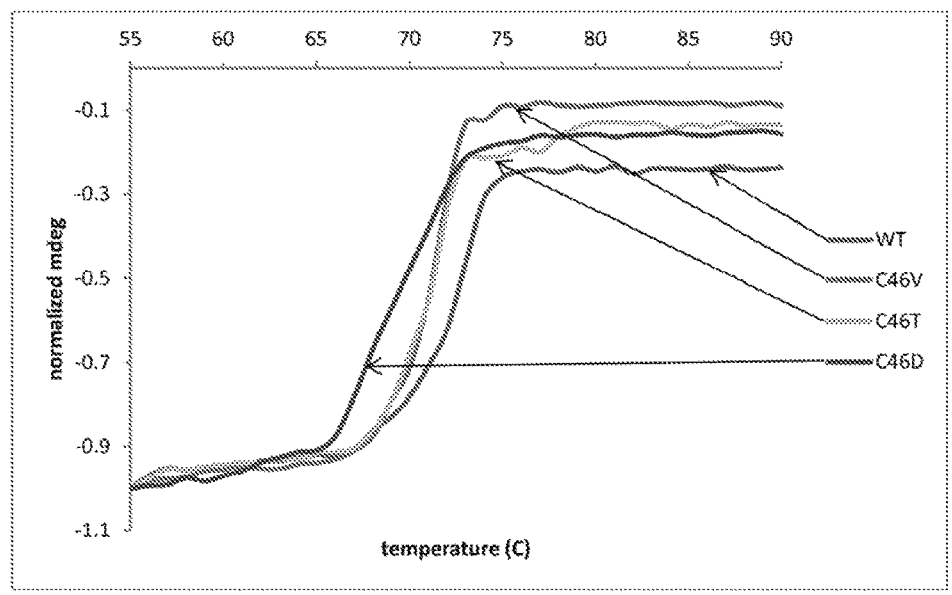
Figure 4C:
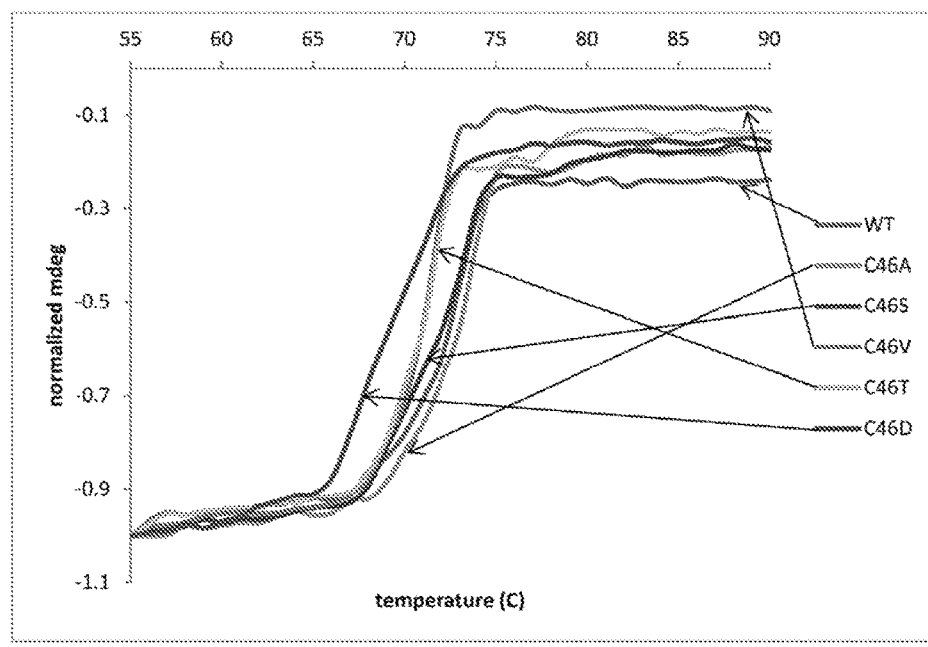

One concern with an engineered protein is that the substitutions made will alter the structural integrity and activity of the protein. Circular diochroism offers a method for investigating subtle secondary structure changes using a direct comparison of the thermal melting curves of the variants to the WT protein. The wild-type *Moorella thermoacetica* cyanuric acid hydrolase is an enzyme from a thermophilic organism, and has been show to melt around 70 C (FIG. 4A). C46S and C46A exhibit thermal melting curves that very closely resemble the WT curve (FIG. 4A). On the other hand, the C46T and V mutants showed a slight reduction in thermal melting point, and the C46D mutant exhibited a more pronounced deviation from the WT curve (FIG. 4B).

Figure 5:
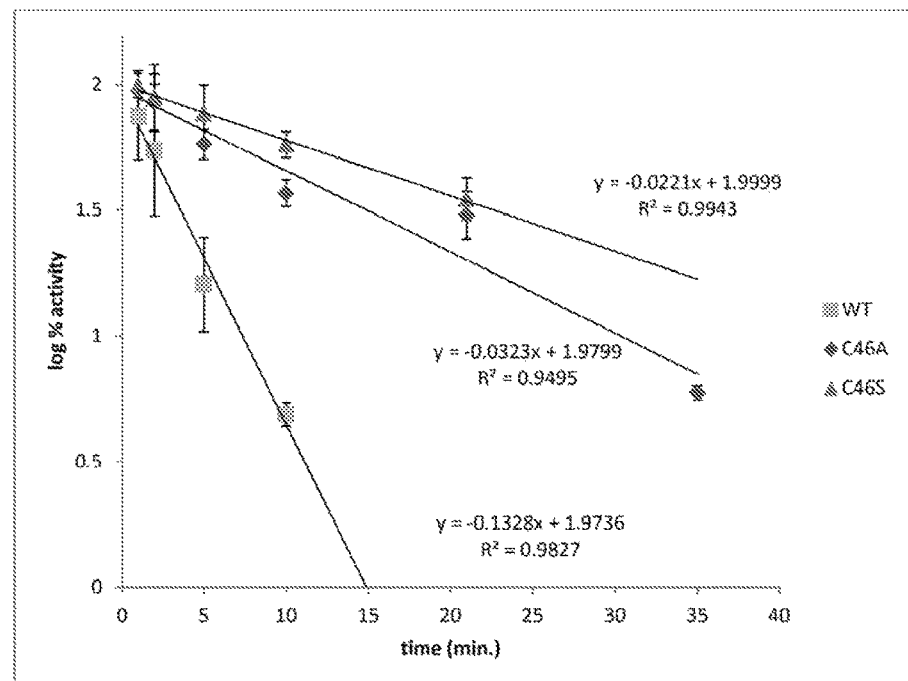
FIG. 5. Evaluation of Moorella CAH (30 μM) WT, C46A and C46S resistance to 8.5 mM $H_2O_2$.

Sensitivity of Engineered CAHs to Additional Oxidants and Sulfhydryl Reactive Reagents To further examine the effect of substitutions at cysteine 46 in *Moorella thermoacetica* cyanuric acid hydrolase (CAH) on the sensitivity of the enzyme to a variety of commonly used oxidants, the sensitivity of the wild-type and variant CAH proteins (C46A and C46S) to hydrogen peroxide ($H_2O_2$), potassium permanganate ($KMnO_4$) and ozone ($O_3$) were compared. It was found that substitution of cysteine 46 to alanine or serine decreases sensitivity of CAH to hydrogen peroxide over four-fold (FIG. 5).

To determine the effect of an additional oxidant, ozone, on the activity of CAH, wild-type CAH was incubated with 1 ppm ozone. This ozone concentration is the upper limit recommended by the EPA for water treatment facilities (EPA Guidance Manual Alternative Disinfectants and Oxidants, April 1999). The enzyme activity was not affected by incubation with ozone.

Figure 6:
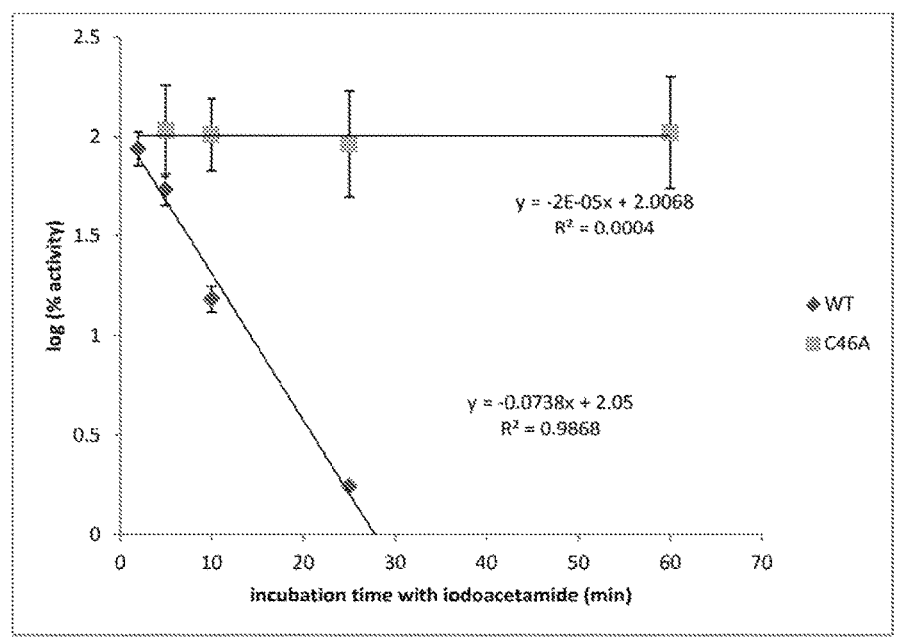
FIG. 6. Evaluation of Moorella CAH (30 μM) WT and C46A resistance to 20 mM iodoacetamide.
Figure 7:
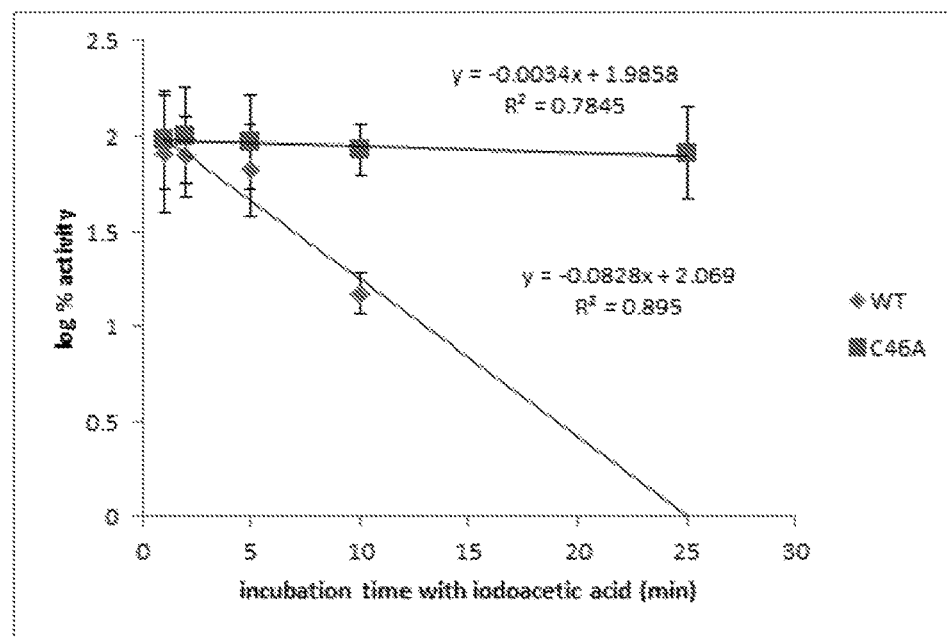
FIG. 7. Evaluation of Moorella CAH (30 μM) WT and C46A resistance to 100 μM iodoacetic acid.

In addition to commonly used oxidants, the effect of a commonly used sulfhydryl reactive agent (iodoacetamide) was also tested on the activity of WT and variant CAH. It was reasoned that a sulfhydryl reactive compound might react with the cysteine sulfhydryl group of the wild-type protein to block substrate access to the active site much in the same way an oxidant could oxidize the cysteine sulfhydryl group and block active site access. It was found that while wild-type CAH (30 uM) activity is greater than 90% inactivated by 20 mM iodoacetamide after 25 minutes, the activity of the C46A variant is not affected by the sulfhydryl reactive agent (FIG. 6).

The effect of a common heavy metal, mercury, on the activity of WT and variant CAH was also tested. Mercury typically inactivates proteins; however, it was found that the mutant CAH enzyme conferred resistance to this heavy metal. Specifically, mercury (II) salts were used to test resistance, which are known to be particularly damaging to proteins. The WT or C46A enzymes (48 uM) were incubated with 1.6 mM phenyl mercuric acetate; the WT CAH enzyme retained 1% activity (+/−13% error) (so it was 99% inactivated) while the C46A mutant enzyme retained 89% activity (+1-11%) (so it was completely resistant within experimental error) when assayed after one minute.

Figure 8:
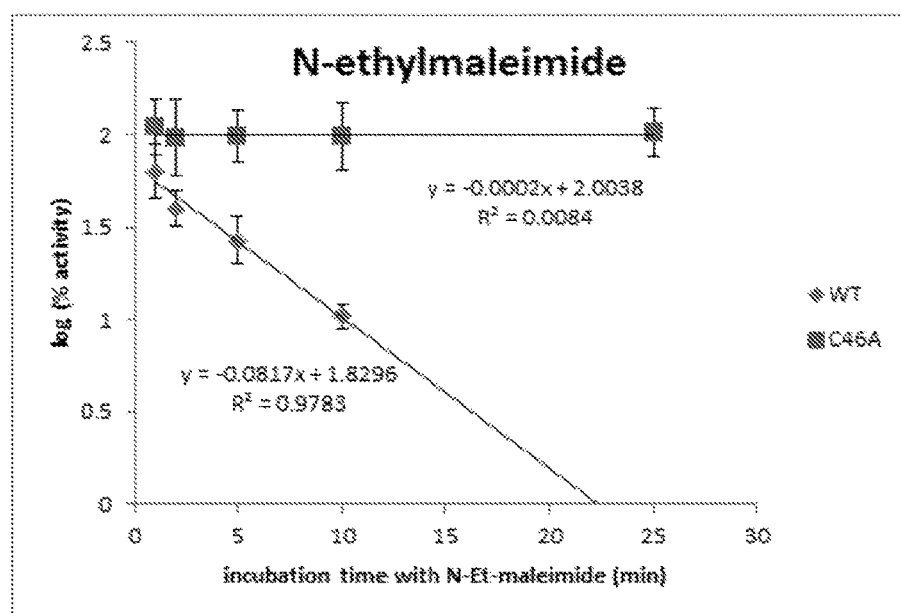
FIG. 8. Evaluation of *Moorella* CAH (30 µM) WT and C46A resistance to 350 µM N-ethylmaleimide.

Inactivation of the WT and variant CAH from a Michael addition reaction was also investigated using N-ethylmaleimide. Specifically, the WT or C46A enzymes (30 uM) were incubated with 350 uM N-ethylmaleimide. It was found that the mutation (C46A) completely protected the CAH enzyme from inactivation, whereas inactivation of the wild-type enzyme was observed in less than a half-hour (FIG. 8).

Methods

Site Directed Mutagenesis

To construct plasmids for expression of *Moorella* CAH variants, mutations were introduced into a pET28-CAH construct (Seffernick et al. 2012) using Stratagene QuikChange II kit per manufacturer instructions. Primers are provided in Table 2.

TABLE 2

Primer pairs used in site-directed mutagenesis.

| Substitution Introduced | Primer Sequence (5' to 3') |
|---|---|
| C46A | Gagtaaaatcgttaacag (SEQ ID NO: 6) caccattaccttccgtcttgccc gggcaagacggaaggtaat (SEQ ID NO: 7) ggtgctgttaacgattttactc |
| C46S | cgagtaaaatcgttaacac (SEQ ID NO: 8) taccattaccttccgtcttg caagacggaaggtaat (SEQ ID NO: 9) ggtagtgttaacgattttactcg |
| C46D | cgagtaaaatcgttaac (SEQ ID NO: 10) atcaccattaccttccgtcttgccca tgggcaagacggaaggtaa (SEQ ID NO: 11) tggtgatgttaacgattttactcg |
| C46V | cgagtaaaatcgttaac (SEQ ID NO: 12) aacaccattaccttccgtcttgccca tgggcaagacggaaggtaa (SEQ ID NO: 13) tggtgttgttaacgattttactcg |
| C46T | gagtaaaatcgttaacagt (SEQ ID NO: 14) accattaccttccgtcttgccc gggcaagacggaaggtaa (SEQ ID NO: 15) tggtactgttaacgattttactc |

Protein Expression and Purification

*E. coli* BL21 with pET28-CAH was grown in the Biotechnology Resource Center, University of Minnesota. A 44 L culture was prepared in T7 medium (yeast extract 23.97 g/L, $K_2HPO_4$ 2.65 g/L, $KH_2PO_4$ 6.72 g/L, $(NH_4)_2SO_4$ 1.36 g/L, citric acid monohydrate 0.73 g/L, ferric chloride hexahydrate 0.19 g/L, glycerol 10.0 g/L, antifoam 204 0.2 g/L, 1M MgSO4-7H2O 2.95 mL/L, kanamycin 50 mg/L, 50% glucose 16 mL/L) pH 6.9, 37° C. in a 75 L New Brunswick Scientific bioreactor. The culture was induced at $A_{600}$ 62 with 0.5 mM isopropyl-β-d-thiogalactopyranoside (IPTG). At 12 hr post-induction ($A_{600}$ 104), cells were harvested, lyophilized and stored at −80° C.

Small scale growth of *E. coli* BL21 for C46 substituted CAH variant protein purification was conducted in 2-liter flasks containing 1 L of LB with 50 µg/ml kanamycin and induced at an $A_{600}$ of 0.4-0.8 with 0.25 mM IPTG at 30 C. After 3 h, cells were harvested by centrifugation for 10 min at 5000×g.

Cells from 2 L pellets or 7 g lyophilized cells paste were suspended and lysed in 20 mL Buffer A (50 mM Tris pH 7.2, 200 mM NaCl). Cells were lysed by three passes through a French press at 1000-1500 p.s.i. The sample was clarified by centrifugation at 48,000 RCF for 40 min and passed through a 0.45 µm filter prior to loading a 5 mL His-Trap HP nickel column (GE Healthcare) pre-equilibrated with Buffer A (50 mM Tris-HCl pH 7.2, 200 mM NaCl) and eluted with a imidazole gradient. Fractions containing CAH were buffer exchanged to remove imidazole using Amicon 10 k or 30 k centrifugal filter units Cyanuric Acid Hydrolase Activity To determine CAH activity, 0.03 µM enzyme was incubated with a 140 ppm cyanuric acid (CYA) solution in phosphate buffered saline (138 mM NaCl, 3 mM KCl, 10 mM $Na_2HPO_4$, 2 mM $KH_2PO_4$). For the WT protein and the C46A and C46S variants, fractions were removed every 5 minutes to assay CYA concentration using a modified melamine turbidity assay (Downes et al. 1984). An equal volume of melamine solution (2.5 mg/mL in water) was added to cyanuric acid samples and mixed thoroughly. The absorbance at 600 nm was read 2 minutes after mixing. For the severely impaired CAH proteins (C46D, V and T), 0.12 µM protein was used and fractions were removed every hour for CYA measurement. Specific activity (nmol $min^{-1}$ $mg^{-1}$) was calculated as the average of triplicate data at two time points.

Bleach Sensitivity

To determine bleach sensitivity of WT, C46A and C46S CAH, purified protein (30 µM) was pre-incubated with or without 1 mM bleach. At appropriate time points, aliquots of the protein samples were diluted 100 fold into a solution of 140 ppm cyanuric acid and incubated for 10 minutes before the cyanuric acid concentration was measured with the melamine turbidity assay. The results are plotted as the log of the percent of untreated-protein activity as a function of treatment time.

Circular Dichroism

The circular dichroism (CD) measurements were performed on a Jasco J-815 spectrometer with 25 µM protein in 50 mM M Tris-HCl buffer, pH 7.2 in a 1 mm path length cell. For thermal melting, the changes in CD spectra at of the proteins were sampled at 220 nm every 1° C. during continuous heating the solutions from 55 to 90° C. at 1 degree per minute. Data were normalized to the initial reading at 55 C.

Sensitivity of Various Oxidant and Sulfhydryl Reagents

To determine sensitivity of WT, C46A and C46S CAH to various oxidants or sulfhydryl reagents, purified protein (30 µM) was pre-incubated with or without the potential inhibitor, 8.5 mM hydrogen peroxide, 50 µM potassium permanganate, 22 µM (1 ppm) ozone or 20 mM iodoacetamide. At appropriate time points, aliquots of the protein samples were diluted 100 fold into a solution of 140 ppm cyanuric acid and incubated for 10 minutes before the cyanuric acid concentration was measured with the melamine turbidity assay (explained in previous document). The results are plotted as the log of the percent of untreated-protein activity as a function of treatment time.

REFERENCES

Cho, S., Shi, K., Seffernick, J. L., Dodge, A. G., Wackett, L. P., and Aihara, H. (2014). Cyanuric acid hydrolase from *Azorhizobium caulinodans* ORS 571: crystal structure and insights into a new class of Ser-Lys dyad proteins. PLoS One 9, e99349.

Downes, C. J., Mitchell, J. W., Viotto, E. S., and Eggers, N. J. (1984). Determination of cyanuric acid levels in swimming pools waters by UV absorbance, HPLC and melamine cyanurate precipitation. Water Research 18, 277-280.

Peat, T. S., Balotra, S., Wilding, M., French, N. G., Briggs, L. J., Panjikar, S., Cowieson, N., Newman, J., and Scott, C. (2013). Cyanuric acid hydrolase: evolutionary innovation by structural concatenation. Mol Microbiol 88, 1149-1163.

Seffernick, J. L., Erickson, J. S., Cameron, S. M., Cho, S., Dodge, A. G., Richman, J. E., Sadowsky, M. J., and Wackett, L. P. (2012). Defining sequence space and reaction products within the cyanuric acid hydrolase (AtzD)/ barbiturase protein family. J Bacteriol 194, 4579-4588.

Cho S, Shi K, Wackett L P, Aihara H. Crystallization and preliminary X-ray diffraction studies of cyanuric acid hydrolase from *Azorhizobium caulinodans*. Acta Crystallogr Sect F Struct Biol Cryst Commun. 2013, 69(Pt 8):880-3.

Li Q, Seffernick J L, Sadowsky M J, Wackett L P. Thermostable cyanuric acid hydrolase from *Moorella thermoacetica* ATCC 39073. Appl Environ Microbiol. 2009, 22, 6986-91.

Although the foregoing specification and examples fully disclose and enable the present invention, they are not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A hypochlorite resistant cyanuric acid hydrolase (CAH) enzyme comprising an amino acid sequence having at least 70% sequence identity to SEQ ID NO:1, SEQ ID NO:3, SEQ ID NO:4 or SEQ ID NO:5, wherein the amino acid sequence comprises an alanine, serine, glycine, dehydroalanine, homoserine or an amino acid having a cyclopropyl or an ethyl side chain at residue 46.

2. The CAH enzyme of claim 1, wherein the amino acid sequence has at least 90% sequence identity to SEQ ID NO:1, SEQ ID NO:3, SEQ ID NO:4 or SEQ ID NO:5.

3. The CAH enzyme of claim 1, wherein the amino acid sequence has at least 95% sequence identity to SEQ ID NO:1, SEQ ID NO:3, SEQ ID NO:4 or SEQ ID NO:5.

4. A hypochlorite resistant cyanuric acid hydrolase (CAH) enzyme comprising an amino acid sequence having at least 70% sequence identity to SEQ ID NO:1, SEQ ID NO:3, SEQ ID NO:4 or SEQ ID NO:5, wherein the amino acid sequence comprises an amino acid at residue 46 that does not block access to the active site of the enzyme and that does not react with hypochlorite to form a reaction product that blocks access to the active site of the enzyme.

5. A hypochlorite resistant cyanuric acid hydrolase (CAH) enzyme comprising an amino acid sequence having at least 70% sequence identity to SEQ ID NO:1, SEQ ID NO:3, SEQ ID NO:4 or SEQ ID NO:5, wherein the amino acid sequence comprises a non-oxidizable amino acid at residue 46.

6. The CAH enzyme of claim 5, wherein the side chain of the non-oxidizable amino acid is less than or about 109 Angstrom$^3$.

7. The CAH enzyme of claim 1, wherein the amino acid sequence comprises SEQ ID NO:3, SEQ ID NO:4 or SEQ ID NO:5.

8. The CAH enzyme of claim 1, wherein the amino acid sequence consists of SEQ ID NO:3, SEQ ID NO:4 or SEQ ID NO:5.

9. The CAH enzyme of claim 1, wherein the CAH enzyme is an isolated or purified CAH enzyme.

10. The CAH enzyme of claim 1, wherein the CAH enzyme is resistant to hydrogen peroxide, an alkylating agent, a heavy metal and/or inactivation from a Michael addition reaction.

11. An isolated or purified nucleic acid encoding a CAH enzyme of claim 1.

12. An expression cassette comprising the nucleic acid of claim 11 and a promoter.

13. A vector comprising the expression cassette of claim 12.

14. A cell comprising the vector of claim 13.

15. A composition for remediation of a liquid comprising a CAH enzyme of claim 1 and a matrix.

16. The composition of claim 15, wherein the liquid is water.

17. A device for remediation of a liquid comprising a matrix and a CAH enzyme of claim 1.

18. The device of claim 17, wherein the device further comprises 1) at least one casing or housing for the matrix, wherein water flows through the at least one casing or housing and contacts the enzyme; and/or 2) a permeable layer.

19. A method of remediating a liquid comprising contacting a liquid from a circulating reservoir with a CAH enzyme as described in claim 1, to reduce the concentration of cyanuric acid in the liquid.

20. The CAH enzyme of claim 1, wherein the amino acid sequence consists of SEQ ID NO:3.

21. The CAH enzyme of claim 1, wherein the amino acid sequence consists of SEQ ID NO:4.

22. The CAH enzyme of claim 1, wherein the amino acid sequence consists of SEQ ID NO:5.

23. A composition for remediation of a liquid comprising a CAH enzyme of claim 4 and a matrix.

24. A device for remediation of a liquid comprising a matrix and a CAH enzyme of claim 4.

25. A method of remediating a liquid comprising contacting a liquid from a circulating reservoir with a CAH enzyme as described in claim 4, to reduce the concentration of cyanuric acid in the liquid.

26. A composition for remediation of a liquid comprising a CAH enzyme of claim 5 and a matrix.

27. A device for remediation of a liquid comprising a matrix and a CAH enzyme of claim 5.

28. A method of remediating a liquid comprising contacting a liquid from a circulating reservoir with a CAH enzyme as described in claim 5, to reduce the concentration of cyanuric acid in the liquid.

* * * * *